US009090662B2

(12) United States Patent
Raines et al.

(10) Patent No.: US 9,090,662 B2
(45) Date of Patent: Jul. 28, 2015

(54) DITHIOAMINE REDUCING AGENTS

(71) Applicant: WISCONSIN ALUMNI RESEARCH FOUNDATION, Madison, WI (US)

(72) Inventors: Ronald T. Raines, Madison, WI (US); John Lukesh, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/768,937

(22) Filed: Feb. 15, 2013

(65) Prior Publication Data
US 2013/0211055 A1   Aug. 15, 2013

Related U.S. Application Data

(60) Provisional application No. 61/599,380, filed on Feb. 15, 2012.

(51) Int. Cl.
| | | |
|---|---|---|
| A61K 38/00 | (2006.01) | |
| C07K 1/113 | (2006.01) | |
| C12N 9/96 | (2006.01) | |
| C07D 339/08 | (2006.01) | |
| C07C 329/16 | (2006.01) | |
| C07C 323/25 | (2006.01) | |
| C07C 327/06 | (2006.01) | |

(52) U.S. Cl.
CPC ............... *C07K 1/113* (2013.01); *C07C 323/25* (2013.01); *C07C 327/06* (2013.01); *C07C 329/16* (2013.01); *C07D 339/08* (2013.01); *C07K 1/1133* (2013.01); *C12N 9/96* (2013.01); *C07B 2200/07* (2013.01)

(58) Field of Classification Search
CPC ..................................................... A61K 38/00
See application file for complete search history.

(56) References Cited

U.S. PATENT DOCUMENTS

| | | | |
|---|---|---|---|
| 4,659,733 | A | 4/1987 | DuPriest et al. |
| 4,755,528 | A | 7/1988 | DuPriest et al. |
| 5,651,960 | A | 7/1997 | Chan et al. |
| 5,910,435 | A | 6/1999 | Raines |
| 2005/0002886 | A1 | 1/2005 | Philippe et al. |

FOREIGN PATENT DOCUMENTS

WO   WO 00/17133   3/2000

OTHER PUBLICATIONS

Kessler et al., Tetrahedron Letters, 1994, vol. 35, No. 39, pp. 7237-7240.*
Cleland (1964) "Dithiothreitol: a new protective reagent for SH groups," Biochemistry. 3:480-482.
Cumming et al. (2004) "Protein Disulfide Bond Formation in the Cytoplasm during Oxidative Stress," J. Biol. Chem. 279:21749-21758.
Evans et al. (1949) "Dithiols. Part III. Derivatives of polyhydric alcohols," J. Chem. Soc. 248-255.
International Search Report with Written Opinion corresponding to International Patent Application No. PCT/US2013/026418, mailed Apr. 19, 2013.
Kessler et al. (Sep. 26, 1994) "Design and synthesis of a novel site-directed reducing agent for the disulfide bond involved in the acetylcholine binding site of the AChoR," Tetrahedron Letters. 35(39):7237-7240.
Lamoureux et al. (Jan. 1993) "Synthesis of Dithiols as Reducing Agents for Disulfides in Neutral Aqueous Solutions and Comparison of Reduction Potentials," J. Org. Chem. 58:633-641.
Lees et al. (Dec. 1, 1991) "Meso-2,5-Dimercapto-N,N,N',N'-tetramethyladipamide: A readily available, kinetically rapid reagent for the reduction of disulfides in aqueous solution," J. Org. Chem. 56:7328-7331.
Oetke et al. (Feb. 22, 2002) "Versatile Biosynthetic Engineering of Sialic Acid in Living Cells Using Synthetic Sialic Acid Analogues," J. Biol. Chem. 277:6688-6695.
Ranganathan et al. (1991) "Highly efficient propane-1,3-dithiol mediated thiol-disulphide interchange: A facile and clean methodology for S—S reduction in peptides," Chem. Commun. 934-936.
Rothwarf et al. (Sep. 1992) "Equilibrium and Kinetic Constants for the Thiol-Disulfide Interchange Reaction Between Glutathione and Dithiothreitol," Proc. Natl. Acad. Sci. USA. 89:7944-7948.
Structure Search Result for 1,2-dithian-4-amine, (4S) providing reference to possible commercial source for the compound and a catalog published on Aug. 16, 2013.
Servent et al. (Mar. 6, 1995) "Site-directed disulfide reduction using an affinity reagent: Application on the nicotinic acetylcholine receptor," FEBS Letters. 360:261-265.
Singh et al. (Mar. 1994) "Reagents for Rapid Reduction of Native Disulfide Bonds in Proteins," Bioorg. Chem. 22:109-115.
Singh, R.; Lamoureux, G. V.; Lees, W. J.; Whitesides, G. M. Methods Enzymol. 1995, 251, 167-173.
Smith et al. (Feb. 1975) "Simple alkanethiol groups for temporary sulfhydryl groups of enzymes," Biochemistry. 14:766-771.
Whitesides et al. (Jan. 1977) "Rates of Thiol-Disulfide Interchange Reactions between Mono- and Dithiols and Ellman's Reagent," J. Org. Chem. 42:332-338.

\* cited by examiner

*Primary Examiner* — Marcela M Cordero Garcia
*Assistant Examiner* — Kaipeen Yang
(74) *Attorney, Agent, or Firm* — Lathrop & Gage LLP

(57) ABSTRACT

Dithioamine reducing agents useful for the reduction of disulfide bonds. The reducing agents of this invention are useful, for example, to reduce disulfide bonds, particularly in proteins, or to prevent the formation of disulfide bonds, particularly in proteins and other biological molecules. Reducing agents of this invention are useful and suitable for application in a variety of biological applications, particularly as research and synthetic reagents. The invention provides S-acylated dithioamines which can be selectively activated reducing agents by removal of the S-acyl groups enzymatically or chemically. The invention further provides dithiane precursors of thioamino reducing agents. The invention provides dithioamine reducing agents, S-acylated dithioamines and dithianes which are immobilized on surfaces, including among others, glass, quartz, microparticles, nanoparticles and resins.

31 Claims, 6 Drawing Sheets

DITHIOAMINE REDUCING AGENTS

CROSS-REFERENCE TO RELATED APPLICATIONS

This application claims the benefit of U.S. provisional application 61/599,380, filed Feb. 15, 2012, which is incorporated by reference herein in its entirety.

STATEMENT REGARDING GOVERNMENT FUNDING

This invention was made with government support under GM044783 awarded by the National Institutes of Health. The government has certain rights in the invention.

BACKGROUND OF THE INVENTION

Approximately 20% of human proteins are predicted to contain disulfide bonds between cysteine residues. [1] Small-molecule thiols can reduce these (and other) disulfide bonds, thereby modulating biomolecular function. [2] The reaction mechanism involves thiol-disulfide interchange initiated by a thiolate. [3] The ensuing mixed disulfide, however, can become trapped if the reagent is a monothiol, such as β-mercaptoethanol (βME). [4]

To overcome this problem, Cleland developed racemic (2S,3S)-1,4-dimercaptobutane-2,3-diol (dithiothreitol or DTT; Table 1), a dithiol that resolves a mixed disulfide by forming a six-membered ring. [2a, 5] DTT is a potent reducing agent ($E^{o\prime}$—0.327 V) [2g] and has been, despite its high cost, the preferred reagent for the quantitative reduction of disulfide bonds and is now the standard reagent for reducing disulfide bonds in biological molecules. [6, 7] At physiological pH, DTT is, however, a sluggish reducing agent. The reactivity of a dithiol is governed by the lower of its two thiol $pK_a$ values. [2, 3] With its lower thiol $pK_a$ value being 9.2, [Table 1] greater than 99% of DTT thiol groups are protonated at pH 7 and thus unreactive (i.e., less than 1% of DTT residues are in the reactive thiolate form at pH 7 [8])

Thus, there is a need in the art for reducing agents useful in biological systems, for example, for the reduction of disulfide bonds, which exhibit properties improved over those of prior art reducing agents. The present invention provides dithiol amines which can be prepared from inexpensive starting materials in high yield and which exhibit desirable improved properties as reducing agents.

SUMMARY OF THE INVENTION

The present invention provides improved dithioamine reducing agents useful, in particular, for the reduction of disulfide bonds. The reducing agents of this invention are useful, for example, to reduce disulfide bonds, particularly in proteins, or to prevent the formation of disulfide bonds, particularly in proteins and other biological molecules (e.g., thiolated species, such as thiolated nucleic acids). Reducing agents of this invention can be employed to regulate protein function in proteins in which a sulfhydryl group (such as those of cysteine residues) is associated with biological activity. Reducing agents of this invention can prevent inactivation of a given protein or enhance activation of a given protein or other biological molecule in vitro and/or in vivo. Reducing agents of this invention can prevent or reduce oxidation of cysteine residues in proteins and prevent the formation of reduced activity protein dimers (or other oligomers). Reducing agents of this invention are useful and suitable for application in a variety of biological applications, particularly as research and synthetic reagents. In specific embodiments, the invention provides S-acylated dithioamines which can be selectively activated as reducing agents by removal of the S-acyl groups enzymatically or chemically. In specific embodiments, the invention provides dithioamine reducing agents and S-acylated dithioamines which are immobilized on surfaces, including among others, glass, quartz, microparticles and nanoparticles.

In specific embodiments, dithioamine reducing agents of this invention exhibit a thiol $pK_a$ value less than 9.2, preferably less than 9.0 and more preferably less than 8.5. In specific embodiments, dithioamine reducing agents of this invention exhibit disulfide reduction potential more negative than −0.28 V, preferably more negative than −0.30 V and more preferably more negative than −0.32 V. In specific embodiments, the dithiol reducing agent contains an amine-containing group substituted on a carbon alpha to the carbon upon which a thiol is substituted. In a specific embodiment, the $pK_a$ of the amine containing group which is substituted on a carbon alpha to a carbon upon which a thiol is substituted is greater than the $pK_a$ of the thiol groups in the reducing agent. In a specific embodiment, the $pK_a$ of this amine-containing group is 10 or greater. In a more specific embodiment, the $pK_a$ of this amine-containing group is 10.5 or greater.

Reducing agents of this invention include compounds of formula I and salts thereof:

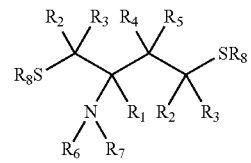

where:

$R_1$ is hydrogen, or an unsubstituted alkyl group having 1 to 3 carbon atoms; each $R_2$ and $R_3$ is independently hydrogen, an alkyl group having 1-3 carbon atoms, a phenyl or a benzyl group, wherein each alkyl, phenyl, or benzyl group is optionally substituted with one or more non-hydrogen substituents;

each $R_4$ and $R_5$ is independently hydrogen, a halogen, a cyano group, a nitro group, a hydroxyl, an alkyl group having 1-6 carbon atoms, a phenyl, a benzyl group, an —N($R_9$)$_2$, or a —COR$_{10}$ group, wherein each alkyl, phenyl, or benzyl group is optionally substituted with one or more of non-hydrogen substituents;

each $R_6$ and $R_7$ is independently hydrogen, a 1-12 carbon alkyl group, an aryl group, a heterocyclic group, a heteroaryl group, a —COR$_{11}$ group, a —CO—NHR$_{11}$ group, a —CO—NHR$_{11}$ group, a —SO$_2$—R$_{11}$ group, or a —(CH$_2$)$_n$—R$_{12}$ group, wherein each alkyl, aryl heterocyclic or heteroaryl group is optionally substituted with one or more non-hydrogen substituents;

each $R_8$ is independently hydrogen or an acyl group (—CO—R$_{13}$), wherein:

each $R_9$ is independently hydrogen, an alkyl group having 1-12 carbon atoms, an aryl group, a heterocyclic group, a heteroaryl group, a —COR$_{11}$ group, a —COOR$_{11}$ group, a —CO—NHR$_{11}$ group, a —CO—NHR$_{11}$ group, a —SO$_2$—R$_{11}$ group, or a —(CH$_2$)$_n$—R$_{12}$ group, where n is an integer ranging from 1-12, wherein each alkyl, aryl, heterocyclic or heteroaryl group is optionally substituted with one or more non-hydrogen substituents;

each $R_{10}$ is independently hydrogen, an alkyl group having 1-12 carbon atoms, a phenyl or benzyl group, wherein each alkyl, phenyl or benzyl group is optionally substituted with one or more of non-hydrogen substituents;

each $R_{11}$ and $R_{12}$ is independently hydrogen, an alkyl group having 1-12 carbon atoms, an aryl group, a heterocyclic group, a heteroaryl group, a -L-T group or a -M group, wherein each alkyl, aryl, heterocyclic or heteroaryl group is optionally substituted with one or more non-hydrogen substituents; -L- is a divalent linker group and T is a biological species or a surface to which the reducing agent is linked; and -M is a reactive group or a spacer moiety carrying a reactive group; and each $R_{13}$ is independently hydrogen, an alkyl group having 1-12 carbon atoms, an aryl group, a heterocyclic group, or a heteroaryl group, wherein each alkyl, aryl heterocyclic or heteroaryl group is optionally substituted with one or more non-hydrogen substituents In specific embodiments, the —$NR_6R_7$ group retains positive charge under application conditions. In specific embodiments, application conditions include use in vivo or in vitro at a pH between 5.5-8.5, between 6 to 8, between 7 to 8, or between 7.2 to 7.6. In specific embodiments, the —$NR_6R_7$ group is protonated under application conditions. Retention of a positive charge on this nitrogen is believed to be beneficial to activity of the reducing agent. In specific embodiments, both of $R_6$ and $R_7$ are groups other than hydrogen, e.g., one of $R_6$ or $R_7$ is an alkyl group and one or $R_6$ or $R_7$ is an —$COR_{13}$ group as defined above.

In a specific embodiment, dithioamine compounds of the invention include compounds of formula IA and salts thereof:

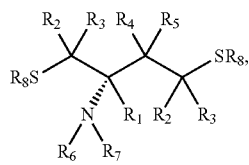

where the optical configuration at the indicated chiral center is as indicated in the formula and variables are as defined above.

Compounds of the invention also include those of formula IB and salts thereof:

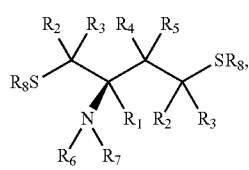

where the optical configuration at the indicated chiral center is as indicated in the formula and variables are as defined above.

In specific embodiments of formulas IA and IB, all of $R_1$-$R_8$ are hydrogens and the compounds are S-2-amino-1,4-dimercaptobutane (S-dithiobutylamine, S-DTBA) or R-2-amino-1,4-dimercaptobutane (R-dithiobutylamine, R-DTBA) or salts thereof, such as the hydrochloride salts thereof.

The invention further relates to the dithiane compounds and salts thereof of formula II which are the oxidized form of the dithioamines:

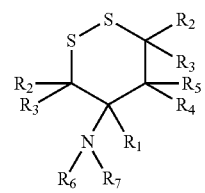

where $R_1$-$R_7$ are as defined above for formula I. In specific embodiments, dithianes of the invention can have the specific optical configuration at the carbon substituted with —$NR_6R_7$ as indicated in formulas IA and IB. In a specific embodiment, dithiane compounds of the invention include the compounds of formula II, with the exception of the compound of formula II, wherein all of $R_1$-$R_7$ are hydrogens. The dithianes are useful, for example, in the preparation of dithioamine reducing agents and particularly in the preparation of immobilized dithioamine reducing agents.

The invention further provides methods for preventing or reducing the oxidation of one or more sulfhydryl groups in a biological molecule, particularly a peptide or protein, in vivo or in vitro by contacting the biological molecule with one or more dithioamine compounds of formulas I, IA or IB. In a specific embodiment, an S-acylated dithioamine of formula I, IA or IB is employed and is activated chemically or enzymatically by removal of a S-acyl group prior to or at about the same time as the protein is contacted. In specific embodiments, the invention provides a method for preventing or reducing the formation of disulfide bonds or for cleaving already-formed disulfide bonds in or between one or more molecules containing sulfhydryl groups or disulfide bonds by contacting the one or more molecules with one or more dithioamine compounds of formulas I, IA or IB. In a specific embodiment, an S-acylated dithioamine of formula I, IA or IB is employed and is activated chemically or enzymatically by removal of a S-acyl group prior to or at about the same time as the one or more molecules are contacted.

In a more specific embodiment, the invention provides a method of regulating a biological activity of a protein wherein said biological activity is associated with the presence or absence of a sulfhydryl group or the formation or cleavage of a disulfide bond. In this method, a dithioamine of this invention is employed to prevent or reduce the oxidation of one or more sulfhydryl groups in a protein or to prevent or reduce the formation of a disulfide bond or to cleave an already-formed disulfide bond.

The invention further relates to reagent kits which comprise one or more dithioamines of formulas I, IA, or IB individually packaged therein in selected amounts for use as a reducing agent. More specifically, such kits are for preventing or reducing disulfide bond formation or for cleaving disulfide bonds. Reagent kits may further comprise one or more solvents or other reagents for carrying out a reduction.

Additional embodiments of the invention will be apparent from a review of the drawings, detailed description and the examples herein.

BRIEF DESCRIPTION OF THE DRAWINGS

FIG. 1A shows reduction of oxidized βME (β-mercaptoethanol) where $k_{obs}^{DTBA}/k_{obs}^{DTT}$=3.5 at pH 7.0;

$k_{obs}^{DTBA}/k_{obs}^{DTT}=4.4$ at pH 5.5.

FIG. 2A shows a reduction of papain-Cys35-S—S—CH$_3$, where $k_{obs}^{DTBA}/k_{obs}^{DTT}=14$.

DETAILED DESCRIPTION OF THE INVENTION

Figure 1A:
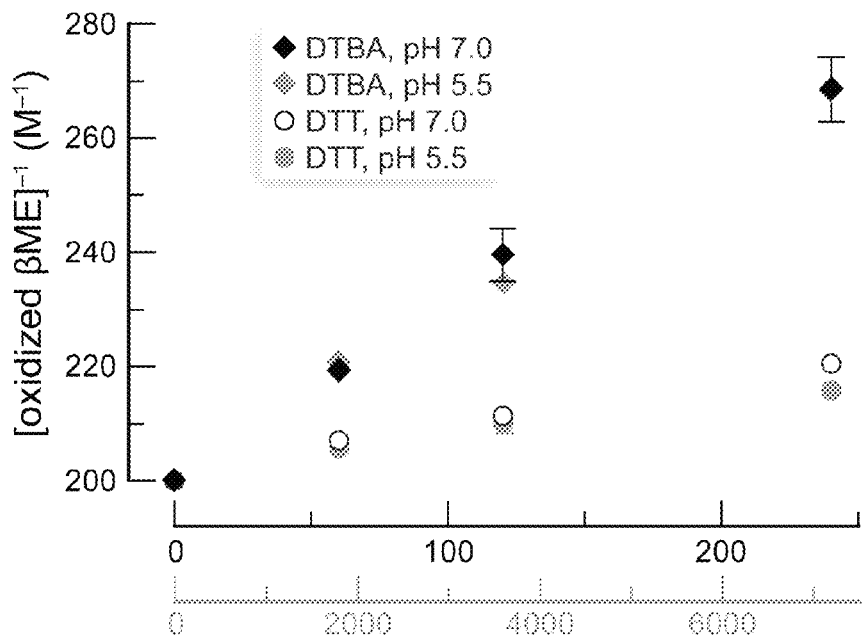
FIGS. 1A and B are graphs illustrating the time-course for the reduction of a mixed disulfide in exemplary small molecules by DTBA and DTT in 50 mM potassium phosphate buffer.

The present invention is based at least in part on the finding that DTBA (specifically S-DTBA) has thiol $pK_a$ values that are significantly lower than those of DTT. DTBA is a non-racemic dithiol with low thiol $pK_a$ and disulfide $E^{o'}$. Additionally DTBA and various derivatives thereof can be prepared from inexpensive sources. DTBA in particular can be prepared in high yield from inexpensive aspartic acid. Various DTBA derivatives can be prepared from derivatives of aspartic acid. The initial target (2S)-2-amino-1,4-dimercaptobutane (dithiobutylamine or DTBA; Table 1) is synthesized from L-aspartic acid, which is an abundant amino acid, see Scheme 1. [9, 10] Salts of the compounds of formulas I, IA and IB can be prepared by art-known methods as illustrated in the examples herein.

The invention provides dithioamine reducing agents of formulas I, IA and IB:

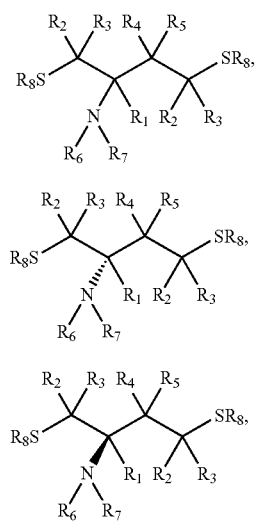

where variables $R_1$-$R_8$ are as defined above and further defined below.

In specific embodiments, the invention provides reducing agents of formulas I, IA and IB which exhibit a thiol $pK_a$ value less than 9.2, preferably less than 9.0 and more preferably less than 8.5. In specific embodiments, the invention provides reducing agents of formulas I, IA or IB which in addition exhibit disulfide reduction potential more negative than −0.28 V, preferably more negative than −0.30 V and more preferably more negative than −0.32 V. In a specific embodiment, the invention provides reducing agents of formulas I, IA and IB in which the $pK_a$ of the —NR$_6$R$_7$ group is greater than the $pK_a$ of the thiol groups in the reducing agent. In a specific embodiment, the $pK_a$ of this —NR$_6$R$_7$ group is 10 or greater. In a more specific embodiment, the $pK_a$ of this —NR$_6$R$_7$ group is 10.5 or greater.

In specific embodiments, when one or more of $R_2$-$R_5$ are an alkyl group having 1-3 carbon atoms, a phenyl or a benzyl group, each alkyl, phenyl, or benzyl group is unsubstituted or is substituted with one or more non-hydrogen substituents selected from substituents $W_2$. In specific embodiments, when $R_{10}$ is an alkyl group having 1-12 carbon atoms, a phenyl or benzyl group, each alkyl, phenyl or benzyl group is unsubstituted or is substituted with one or more non-hydrogen substituents selected from substituents $W_2$.

Substituents $W_2$ are one or more substituents selected from: halogen, an oxo group (=O), cyano group, a nitro group, a hydroxyl, an unsubstituted alkyl group having 1-3 carbon atoms, a halogen-substituted alkyl group having 1-3 carbon atoms, or an unsubstituted alkoxy group having 1-3 carbon atoms.

Preferred $W_2$ substituents are one or more halogen, unsubstituted alkyl or unsubstituted alkoxy. Specific $W_2$ substituents include one or more —CH$_3$, —C$_2$H$_5$, —CF$_3$, —COH, —COCH$_3$, —F, —Cl, —OCH$_3$, or —OC$_2$H$_5$. Substituents $W_2$ includes one, two or three of the listed substituents. In specific embodiments, $R_2$-$R_5$ are not substituted with nitro groups.

In specific embodiments, when one or more of $R_6$, $R_7$, $R_9$, $R_{11}$, $R_{12}$ or $R_{13}$ is a 1-12 carbon alkyl group, an aryl group, a heterocyclic group, or a heteroaryl group, each alkyl, aryl, heterocyclic or heteroaryl group is unsubstituted or is optionally substituted with one or more substituents $W_3$.

Substituents $W_3$ are one or more substituents selected from:
halogen,
an oxo group (=O),
cyano group,
nitro group,
hydroxyl,
an optionally substituted alkyl group having 1-6 carbon atoms,
an unsubstituted alkyl group having 1-6 carbon atoms,
a hydroxyl-substituted alkyl group having 1-6 carbon atoms,
a halogen-substituted alkyl group having 1-6 carbon atoms,
an unsubstituted alkoxy group having 1-6 carbon atoms,
an alkyl group having 2-6 carbon atoms,
an alkyenyl group having 2-6 carbon atoms,
a 3-6-member alicyclic ring, wherein one or two ring carbons are optionally replaced with —CO— and which may contain one or two double bonds,
an aryl group having 6-14 carbon ring atoms,
a phenyl group,
a benzyl group,
a 5- or 6-member ring heterocyclic group having 1-3 heteroatoms wherein one or two ring carbons are optionally replaced with —CO— and which may contain one or two double bonds,
a heteroaryl group having 1-3 heteroatoms (N, O or S), a —CO$_2$R$_{14}$ group,
a —CON(R$_{15}$)$_2$ group,
a —OCON(R$_{15}$)$_2$ group,
a —N(R$_{15}$)$_2$ group,
a —SO$_2$—OR$_{15}$ group,
a —(CH$_2$)$_m$—OR$_{14}$ group, or
a —(CH$_2$)$_m$—N(R$_{15}$)$_2$ group,
where m is 1-8, each R$_{14}$ is hydrogen; an unsubstituted alkyl group having 1-6 carbon atoms; an unsubstituted aryl group having 6-14 carbon atoms; an unsubstituted phenyl group; an unsubstituted benzyl group; an unsubstituted 5- or 6-member ring heterocyclic group, having 1-3 heteroatoms and wherein one or two ring carbons are optionally replaced with —CO— and which may contain one or two double bonds; or a unsubstituted heteroaryl group having 1-3 heteroatoms (N, O or S); and each R$_{15}$ is hydrogen; an unsubstituted alkyl group having 1-6 carbon atoms; an unsubstituted aryl group having 6-14 carbon atoms; an unsubstituted phenyl group; an unsubstituted benzyl group; an unsubstituted 5- or 6-member ring heterocyclic group, having 1-3 heteroatoms and wherein one or two ring carbons are optionally replaced with —CO— and which may contain one or two double bonds; or a unsubstituted heteroaryl group having 1-3 heteroatoms (N, O or S).

Preferred W$_3$ substituents are halogen, hydroxyl, oxo group (=O), a cyano group, a nitro group, unsubstituted and substituted alkyl groups as defined above, unsubstituted alkoxy, unsubstituted phenyl or benzyl, and halogen-substituted phenyl or benzyl. Specific W$_2$ substituents include alkyl groups having 1-3 carbon atoms, alkoxy groups having 1-3 carbon atoms, —CH$_3$, —C$_2$H$_5$, —CF$_3$, —COH, —COCH$_3$, —F, —Cl, —OCH$_3$, and —OC$_2$H$_5$. In specific embodiments, R$_6$, R$_7$, R$_9$, R$_{11}$, R$_{12}$ and R$_{13}$ are not substituted with nitro groups.

In a specific embodiment, dithioamine compounds of the invention include the compound of formula I wherein all of R$_1$-R$_8$ are hydrogens, 2-amino-1,4-dimercaptobutane or dithiobutylamine (DTBA) or a salt, such as the hydrochloride salt, thereof.

In specific embodiments, the invention provided S-acylated dithioamines of formulas IC and ID salts thereof and various optical isomers thereof:

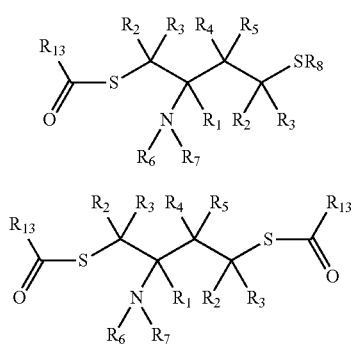

where R$_1$-R$_8$ and R$_{13}$ are as defined above and herein below. These S-acylated dithioamines are precursors of dithioamine reducing agents of this invention. In specific embodiments, R$_{13}$ is an optionally substituted alkyl group having 1-6 carbon atoms, or a an optionally substituted phenyl or benzyl group. In specific embodiments, R$_{13}$ is an unsubstituted, straight-chain alkyl group having 1-6 carbon atoms or 1-3 carbon atoms. In specific embodiments, R$_{13}$ is an unsubstituted, branched alkyl group having 3-6 carbon atoms. In specific embodiments, R$_{13}$ is a hydroxy-substituted alkyl group having 1-6 carbon atoms. In specific embodiments, R$_{13}$ is a butyl group, including all isomers thereof. In specific embodiments, R$_{13}$ is a t-butyl or neopentyl group. In specific embodiments, R$_{13}$ is an unsubstituted phenyl or benzyl group.

Compounds of formulas I, and IA-ID and II include all enantiomers and diastereomers thereof.

In specific embodiments of formulas I, IA and IB each R$_8$ is hydrogen. In specific embodiments of formulas I, IA, IB and II, R$_1$ is hydrogen. In specific embodiments of formulas I, IA, IB and II, each R$_2$ and R$_3$ is independently hydrogen or unsubstituted alkyl groups having 1-3 carbon atoms. In specific embodiments of formulas I, IA, IB and II, each R$_2$ and R$_3$ is a hydrogen. In specific embodiments of formulas I, IA, IB and II, each R$_4$ and R$_5$ is independently hydrogen, a halogen, a cyano group, a nitro group, a hydroxyl, an alkyl group having 1-6 carbon atoms optionally substituted with one or more halogens, or a —COR$_{10}$ group wherein R$_{10}$ is hydrogen or an alkyl group having 1-6 carbon atoms optionally substituted with one or more halogens. In specific embodiments, R$_4$ and R$_5$ are not nitro groups. In specific embodiments, R$_4$ and R$_5$ are both hydrogens.

In specific embodiments of formulas I, IA, IB and II, R$_6$ and R$_7$ are hydrogens or unsubstituted alkyl groups having 1-6 carbon atoms. In specific embodiments of formulas I, IA, IB and II, R$_6$ and R$_7$ are both hydrogens. In specific embodiments of formulas I, IA, IB and II, one of R$_6$ and R$_7$ is a hydrogen. In specific embodiments, one of R$_6$ and R$_7$ is a hydrogen, and the other is a 1-12 carbon alkyl group, an aryl group, a heterocyclic group, a heteroaryl group, a —COR$_{11}$ group or a —(CH$_2$)$_n$—R$_{12}$ group. In specific embodiments, one of R$_6$ and R$_7$ is a —COR$_{11}$ group, a —CO—NHR$_{11}$ group, a —CO—NHR$_{11}$ group, a —SO$_2$—R$_{11}$ group, or a —(CH$_2$)$_n$—R$_{12}$ group, wherein R$_{11}$ or R$_{12}$ is a -L-T group or a -M group.

In specific embodiments, the dithioamine of this invention is substituted with a reactive group which allows its coupling to a biological species or to a surface either directly or indirectly through a spacer moiety. In specific embodiments, the reactive group is a latent reactive group, such as a protected group which can be selectively activated for reaction for coupling of the compound directly or indirectly via a linker or spacer group to a T group or a surface. In specific embodiments, -M is or carries a reactive group or latent reactive group which reacts or can be activated (e.g., by deprotection) to react with one or more of an amine group, a carboxylic acid group, a sulfhydryl group, a hydroxyl group, an aldehyde or ketone group, an azide group, an activated ester group, a thioester group, or a phosphinothioester group or reacts with one reactive group of a homobifunctional or a heterobifunctional crosslinking reagent. In specific embodiments, when the reactive group is a sulfhydryl group, both of R$_8$ are acyl groups.

In specific embodiments, reactive groups are latent reactive groups which are protected amine groups, protected carboxylic acid groups, protected sulfhydryl groups, protected hydroxyl groups, or protected aldehyde or ketone groups. Protective groups, for various reactive groups are known in the art, for example as described in Wutts, P. G. and Greene, T. (2007) Green's Protecting Groups in Organic Synthesis (Fourth Edition) John Wiley & Sons, N.Y. This reference is incorporated by reference herein for its description of protective groups for a given reactive group and for methods of protecting reactive groups and methods for removing such protective groups. One or ordinary skill in the art can select from among known alternatives a protective group appropriate for a given reactive group under given conditions.

Amine-protective groups include among others: t-butyloxycarbo(BOC), 9-fluorenylmethyloxycarbonyl (FMOC), acetyl, benzyl, carbamate, p-methoxyphenyl, tosyl, 4-nitrophenylsulfonyl, or 4-aminophenyl sulfonyl. Carboxylic acid-protective groups include among others, esters (e.g., alkyl or aryl esters of the carboxylic acid), silyl esters, or orthoesters. Hydroxyl-protecting groups include among others, acyl groups (e.g., acetyl, benzoyl), beta-methoxyethoxymethyl ether, dimethoxytrityl, methoxytrityl, methoxymethyl ether, p-methoxybenzyl ether, pivaloyl, silyl ethers, methyl ethers or ethoxyethyl ethers.

In specific embodiments, the dithioamine of this invention is immobilized onto a surface via a linker group -L-. In specific embodiments, the dithioamine of this invention is an S-acylated dithioamine of this invention immobilized onto a surface via a linker group -L-. In specific embodiments, the dithioamine of this invention is conjugated to a biological molecule via a linker group -L-. In specific embodiments, the dithioamine of this invention is an S-acylated dithioamine of this invention conjugated to a biological molecule via a linker group -L-. In specific embodiments, the biological molecule is a peptide or protein, a carbohydrate or a nucleic acid. In specific embodiments, the biological molecule is a ligand or substrate that binds to a biological molecule, particularly where the biological molecule is a peptide or protein.

The invention provides dithioamine reducing agents immobilized on surfaces. Such immobilized reducing agents can be used as recognized in the art to reduce all types of disulfides, particularly biological disulfides, including those in or between proteins. Separation of reduced species from the reducing agent requires less effort and is more efficient. Immobilized reducing agent can be regenerated as is known in the art and reused multiple times. The immobilized dithioamines can be S-acylated (particularly S-acetylated) for chemical or enzymatic activation prior to use. In specific embodiments, preferred S-acylated dithioamines are also N-acylated. For example, S-acylated dithioamines can be deacylated employing hydroxyl amine or other such art-recognized deacylating reagents. The dithioamine reducing agents can be immobilized on any appropriate surface by any immobilization method known in the art. In specific embodiments, dithioamine reducing agents can be covalently attached to a surface by reaction of a reactive group on the reducing agent with a reactive group on the surface. Alternatively, a homo- or heterobifunctional crosslinking reagent such as are known in the art can be employed to immobilize the dithioamine reducing agent of this invention on the surface.

S-acylated dithioamines function as precursors of the dithioamine reducing agents hereof which can be activated as reducing agents by removal of the S-acyl groups to generate sulfhydryl groups. In more preferred embodiments of S-acylated dithioamines, one of $R_6$ or $R_7$ is an acyl group to avoid substantial acyl transfer to the —$NR_6R_7$ group. In other preferred embodiments, both of $R_6$ and $R_7$ are groups other than hydrogen, e.g., one of $R_6$ or $R_7$ is an alkyl group and one or $R_6$ or $R_7$ is an —$COR_{13}$ group as defined above. S-acylated dithioamines of this invention can be activated by removal of acyl groups as is known in the art, for example by treatment with hydroxylamine or by treatment with acidic methanol as illustrated in Scheme 1. Of particular interest is activation of S-acylated dithioamines with esterases, including carboxylesterases. Useful esterases that function for removal of S-acyl groups are known in the art, such as those esterases that are associated with the removal of SATE (S-acyl-2-thioethyl) protection [30, 31, 32].

In a specific embodiment, S-acylated precursors of reducing agents herein are activated in vivo, e.g., inside of cells by the action of esterases therein. For example, these precursors can be activated inside of mammalian cells by the action of mammalian esterase. More specifically, these precursors can be activated inside of human cells by the action of human esterases. It is noted that such esterase may also be employed in vitro for activation of S-acylated precursors.

The invention provides dithioamine reducing agents conjugated to various species T which can be biological molecules, such as proteins, carbohydrates or nucleic acids; labels or tags, such as radiolabels, isotopic labels or fluorescent labels or ligands or substrates that selectively bind to target the conjugate to species which are to be selectively reduced. In specific embodiments, the reducing agents of this invention can be targeted for reduction of a specific protein employing such selective ligands or substrates. In specific embodiments, ligands can be mono- or disaccharides, e.g., glucose or fructose. In specific embodiments, ligands can be sialic acid or analogues thereof (see, exemplary sialic acid analogues in ref. 33). Reference 33 is incorporated by reference herein in its entirety for its description of sialic acid analogues.

As noted above, dithioamine reducing agents of this invention optionally carry -M or -L-T groups which function for immobilization, optionally spacing, and/or conjugation to surfaces or other chemical or biological moieties, i.e., T. In specific embodiments, -M is a reactive group or a spacer moiety or linker (-L-) carrying a reactive group wherein the reactive group reacts with one or more of: an amine group, a carboxylic acid group, a sulfhydryl group, a hydroxyl group, an aldehyde or ketone group, an azide group, an activated ester group, a thioester group, or phosphinothioester, or reacts with one reactive group of a homobifunctional or a heterobifunctional crosslinking reagent. In another embodiment, M is or contains a reactive group that can be ligated to a peptide or protein by a peptide ligation method. In specific embodiments, M is or contains an amine group, a carboxyl group or ester thereof, an activated ester group, an azide, a thioester, or a phosphinothioester. In another embodiment, M is or contains a latent reactive group which can be selectively activated for reaction.

In general the optional spacer moiety of the M group is compatible with the reactive group therein (e.g., does not detrimentally affect reactivity of the reactive group) and the spacer itself is not reactive with the compounds to be conjugated or surfaces on which the reagent is to be immobilized. In specific embodiments, the spacer moiety contains from 3-20 atoms (typically C, O, S and/or N atoms which may be substituted with H or non-hydrogen substituents), including residues from the reactive group), and optionally contains one or more carbon-carbon double bonds, and/or a 5- to 8-member alicyclic, a 5- to 8-member heterocyclic, a 6- or 10-member aryl or a 5- or 6-member heteroaryl ring. Carbon atoms in the spacer or linker are optionally substituted with one or more hydroxyl groups, oxo moieties (=O), or halogens (e.g., F). Nitrogen groups in the spacer may be substituted with hydrogen and/or with C1-C3 alkyl groups. The spacer may contain a diol (>C(OH)—C(OH)<) moiety. The spacer may be selectively cleavable by change of conditions (e.g., pH change), addition of a cleavage reagent, or photo irradiation (e.g., UV irradiation). In specific embodiments, a cleavable spacer includes a diol moiety which is selectively cleavable by treatment for example with periodate, an ester moiety, which is selectively cleavable by treatment with hydroxylamine, or a sulfone moiety (—SO$_2$—) which is selectively cleavable under alkaline conditions.

In specific embodiments, -M selected from —X or -L-X, where X is the reactive group for ligation, bonding or crosslinking to an amino acid, peptide or protein and -L- is a divalent linker or spacer moiety.

A variety of spacer or linker moieties -L- are known in the art to be useful for bioconjugation or immobilization. In specific embodiments, the linker may be a bond. All such art known spacer moieties can be employed in this invention, if compatible with the chemistry of the dithioamine reagent and the species or surface to which the reagents is to be conjugated or upon which it is to be immobilized. The spacer moiety should not detrimentally affect reactivity of chosen reactive groups and should not itself react with the dithioamine reagent, any reactive group employed for conjugation or immobilization or with the surface or species to be conjugated to the reagent.

In specific embodiments -L- is selected from the following divalent moieties:

—Y1-L1-Y3-, where Y1 and Y3 are optional and may be the same or different;

—Y1-L1-L2-Y3-, where Y1 and Y3 are optional and may be the same or different and L1 and L2 are different; or —Y1-L1-[L2-Y2]y-L3-Y3-, where Y1 and Y3 are optional, Y1, Y2 and Y3 may be the same or different, L1 and L3 are optional and L1, L2 and L3 may be the same or different and y is an integer indicating the number of repeats of the indicated moiety;

wherein each L1-L3 is independently selected from an optionally substituted divalent aliphatic, alicyclic, heterocyclic, aryl, or heteroaryl moiety having 1 to 30 atoms and each Y1, Y2 and Y3 is independently selected from: —O—, —S—, —NRc-, —CO—, —O—CO—, —CO—O—, —CO—NRc-, —NRc-CO—, —NRc-CO—NRc-, —OCO—NRc-, —NRc-CO—O—, —N=N—, —N=N—NRc-, —CO—S—, —S—CO—, —SO$_2$—, —CRc(OH)—CRc(OH)—, where Rc is hydrogen or C1-C3 alkyl.

In specific embodiments, y is 1-12 and L1-L3 are selected from: —(CH$_2$)y- (an alkylene) wherein one or more, and preferably 1-4, carbons of the alkylene are optionally substituted with one or more non-hydrogen substituents selected from halogens, C1-C3 alkyl groups or hydroxyl groups, preferred y are 2-6;

a cycloalkylene, having a 3-8-member ring wherein one or more, and preferably 1-4, carbons of the cycloalkylene are optionally substituted with one or more non-hydrogen substituents selected from halogens, C1-C3 alkyl groups or hydroxyl groups, including among others a 1,4-cyclohexylene, a 1,3-cylohexylene, a 1,2-cyclohexylene; a 1,3-cyclopentylene, each of which is optionally substituted;

a phenylene, wherein 1-4 of the ring carbons are optionally substituted with one or more non-hydrogen substituents selected from halogens, C1-C3 alkyl groups, nitro group, cyano group, or hydroxyl groups, including a 1,4-phenylene, a 1,3-phenylene or a 1,2-phenylene, each of which is optionally substituted;

a naphthylene, wherein 1-8 of the ring carbons are optionally substituted with one or more non-hydrogen substituents selected from halogens, C1-C3 alkyl groups, nitro group, cyano group, or hydroxyl groups, including a 2,6-naphthylene, a 2,7-naphthylene, a 1,5-naphthylene, or a 1,4-naphthylene moiety, each of which is optionally substituted;

a biphenylene, wherein 1-8 of the ring carbons are optionally substituted with one or more non-hydrogen substituents selected from halogens, C1-C3 alkyl groups or hydroxyl groups, including a 1,4'-biphenylene, a 1,3'-biphenylene or a 1,2'-biphenylene, each of which is optionally substituted;

an alkenylene, i.e., a divalent alkylene group, containing one or more, preferably 1 or 2 double bonds and having 2-12 and preferably 2-8 carbon atoms, wherein one or more, and preferably 1-4, carbons are optionally substituted with one or more non-hydrogen substituents selected from halogens, C1-C3 alkyl groups or hydroxyl groups, including among others, —CH=CH— and —CH=CH—CH=CH— which are optionally substituted;

a heterocyclene (i.e., a divalent heterocyclic moiety) having a 3-8-member ring with 1-3 heteroatoms, selected from N, O or S, wherein one or more, and preferably 1-4 carbons, or where feasible heteroatoms, of the heterocyclene are optionally substituted with one or more non-hydrogen substituents selected from halogens, C1-C3 alkyl groups, nitro groups, or hydroxyl groups, including among others a 2,4-3H-azepinylene moiety, a piperidinylene (e.g., a 1,4-piperidinylene), a piperazinylene (e.g., a 1,4-piperazinylene), a triazolidinylene (a divalent triazolidinyl) or a triazolylene (a divalent triazolyl) each of which is optionally substituted; or a heteroarylene (i.e., a divalent heteroaryl moiety) having a 5- or 6-member heteroaryl ring having 1-3 heteroatoms selected from N, O or S, wherein one or more, and preferably 1-2 carbons, or where feasible heteroatoms, of the heteroarylene are optionally substituted with one or more non-hydrogen substituents selected from halogens, C1-C3 alkyl groups, nitro groups, or hydroxyl groups, including among others a pyridylene (e.g., 2,5-pyridylene), imidazolylene (e.g., 2,5-imidazolylene, 4,5-imidazolylene), each of which is optionally substituted.

In additional embodiments, the spacer is an ethylene glycol spacer. More specifically, -L- is selected from —[(CH$_2$)y-O]a-, where y is 1-4 and a is 1-6, and preferably 1-3.

In further embodiments, -M is selected from:

—CO—NH—CRaRb—[CO—NH—CRaRb]a-CO—OH, where a is 1-6;

—COO—CRaRb—[CO—NH—CRaRb]a-CO—OH, where a is 1-6;

—O—CO—NH—CRaRb—[NH—CO—CRaRb]a-NH$_2$, where a is 1-6;

—Y4-CRaRb—[W—CRaRb]a-X4, where W is —NH—CO— or —CO—NH—, where a is 1-6;

where:

—X4 is a functional group that reacts with one or more of an amine group, a carboxylic acid group or ester thereof, a sulfhydryl group, a hydroxyl group, an azide group, a thioester group, a phoshinothioester group, an aldehyde group or a ketone group of an amino acid, peptide or protein; and —Y4- is —O—, —S—, —NH—, —CO—, —CO$_2$—, —O—CO—, —CO—O—, —CO—NRc-, —NRcCO—, —CO—S—, or —S—CO— and Rc is hydrogen or a C1-C3 alkyl;

Ra and Rb are selected independently from hydrogen, a C1-C8 aliphatic group, an alicyclic, a heterocyclic, an aryl or a heteroaryl group, each of which is optionally substituted or Ra is hydrogen and Rb is a side-group or protected side-group of a proteinogenic amino acids or an amino acid selected from hydroxyproline, ornithine, or citrulline.

In specific embodiments, X and X4 are —NH$_2$, —COOH or an activated ester thereof, —SH, —N$_3$, —COH, —CO—CH=CH$_2$, —NH—CO—CH=CH, or —C≡CH.

In specific embodiments, the reducing agent of formula I, IA or IB except for the -M group or any salt counterion thereof contains at most 20 carbon atoms.

In specific embodiments, in the reducing agent of formula I, IA or IB, none of $R_1$-$R_5$ or $R_8$ is an —$N(R_9)_2$ group where one or both of $R_9$ is hydrogen or an alkyl group. In specific embodiments, in the reducing agent of formula I, IA or IB, none of $R_1$-$R_5$ or $R_8$ carries an amine group —$N(R_9)_2$ group where one or both of $R_9$ is hydrogen or an alkyl group. In specific embodiments, in the reducing agent of formula I, IA or IB, none of $R_1$-$R_5$ or $R_8$ is a hydroxyl group. In specific embodiments, in the reducing agent of formula I, IA or IB, none of $R_1$-$R_5$ or $R_8$ is substituted with a hydroxyl group.

T is a biological or chemical species or a surface to which a reducing agent is conjugated, typically via a spacer or linking moiety (-L-). T can be a biological molecule, which includes molecules derived from nature such as peptides, proteins, carbohydrates (e.g., mono-, di- and oligosaccharides), or nucleic acids (e.g., a nucleoside, a mono-, di- or polynucleotide, a DNA sequence or an RNA sequence) which may be isolated from nature or synthesized. T can be a biological or chemical species which is a ligand which binds to a biological molecule or which is a substrate for an enzyme. T can, for example, be a biological or chemical species which is anionic or cationic which will preferentially associate with a corresponding cationic or anionic portion, respectively, of a biological molecule, such as a peptide or protein to target the biological molecule and selectively target the reducing agent (or acylated precursor thereof) of this invention to the biological molecule to affect its biological activity.

In a particular embodiment, T is a pharmacophore of a selected biologically active species, particularly a pharmacophore associated with a selected peptide or protein or ligands thereof. As is known in the art, pharmacophore refers to the 3-D molecular features (structural and electronic features) necessary for interaction with a target biological species which can trigger or block a biological response. Pharmacophore modeling [29] represents one aspect of ligand-based drug design which can provide 3-D chemical moieties which interact with biological molecules (e.g., by binding or association therewith) and thereby affect biological function thereof.

In specific embodiments, dithioamines of this invention can be immobilized on various surfaces including inorganic and organic surfaces. The surface may be among others that of a plate, a container (tube, bottle, etc.) which can, for example, be made of plastic or glass, a bead, particle, microparticle or nanoparticle. The surface may be a polymer, a co-polymer, a block co-polymer, a graft-copolymer or a resin each of which may be cross-linked. Polymeric materials include among others, agarose, poly(acrylamide) and co-polymers thereof, poly(methylmethacrylate) and co-polymers thereof, poly(hydroxyethyl methacrylate) and co-polymers thereof, poly(vinyltoluene) and co-polymers thereof, poly(styrene) and co-polymers thereof (e.g., poly(styrene/divinylbenzene) copolymers, poly(styrene/acrylate) co-polymers, poly(styrene/butadiene) co-polymers, poly(styrene/vinyltoluene) co-polymers). The surface may be that of a core-shell particle having a core of one material (e.g., one polymeric material) and a shell or coating of a different material (e.g., a coating polymers, such as poly(ethylene glycol), poly(vinyl alcohol), poly(acrylamide), poly(vinyl pyrrolidone), among others. A specific core-shell particle has a poly(styrene) core with a poly(hydroxyethyl methacrylate) shell.

The surface may be glass, quartz, silica, silica gel, alumina or other metal oxides, or inert metal such as gold (e.g., gold nanoparticles), again in the form among others of plates, beads or particles. The surface may be that of a magnetic, paramagnetic or superparamagnetic material.

The surfaces may contain reactive functional groups that derive from the material from which the particle is made (e.g., OH groups on glass, or amine groups of poly(acrylamide)) or the particles may be functionalized as is known in the art with reactive groups, for example, as noted above, including among others, amine groups, aldehyde or ketone groups, carboxyl groups, epoxides, hydrazides, hydroxyl, amide, sulfamyl groups, or activated esters, such as tosyl-, mesyl- or tresyl-activated esters or NHS esters.) Hermanson, G. T. (2008) Bioconjugate Techniques (Second Edition) Academic Press, N.Y., Chapter 14, pages 582-625 described conjugation/immobilization of various chemical and biological species on surfaces and particles. This reference is incorporated by reference herein in its entirety for this description.

In a specific embodiment, one or more reducing agents of this invention are conjugated to a polymer (i.e., T is a polymer). In a specific embodiment, two or more molecules of reducing agent are conjugated to a polymer. In a specific embodiment, 10% or more or 25% or more of the monomer groups of a polymer are conjugated to a reducing agent of formulas I, IA or IB. In specific embodiments, the polymer carries one or more amino groups which can be conjugated, optionally but preferably via a spacer or linker, to a reducing agent or acylated precursor thereof of this invention. In specific embodiments, the polymer carries one or more amine, amide or ester side chains which can be conjugated to one or more reducing agents of this invention. Polymers useful for such conjugation include among many others, poly(lysine), poly(ornithine), poly(lysine ornithine), poly(aspartic acid), poly(glutamic acid), poly(acrylamide), poly(ethylene imine), poly(propylene imine), poly(allyl amine), poly(vinyl amine), poly(2-aminoethyl methacrylate), poly(methacrylate), poly(methyl methacrylate), poly(acrylate), poly(hydroxyethyl methacrylate), poly(methyl acrylate), poly(vinyl acetate) and copolymers including block copolymers thereof. Methods of conjugation as described in Hermanson, G. T. (2008) Bioconjugate Techniques (Second Edition) Academic Press, N.Y. can be employed or readily adapted for conjugation to polymers.

In specific embodiments, the dithioamine reducing agents or dithiane precursors thereof are covalently attached to surfaces, in particular to resins, which may be in the form of beads or other particles or in the form of coatings on surfaces or particles. In specific embodiments, resins useful for immobilization of dithioamines or dithianes of this invention include resins known and used in the art for solid-phase organic synthesis and/or for solid-phase peptide synthesis. A variety of such resins are known in the art and are commercially available or can be prepared by methods that are well-known in the art. For example, such resins are or may be functionalized with amine, azide, carboxyl, sulfamyl, formyl, halogen, hydroxyl, mercapto, sulfonylchloride, sulfonic acid, or various activated ester groups for reaction with appropriate reactive groups attached to the dithioamine or dithiane to immobilize the dithioamine or dithiane. Resins are typically composed of a polymer matrix which may be cross-linked, such as polystyrene, and functional groups may be directly attached to the resin or attached to a linker groups, such as polyethylene glycol, which are in turn attached to the resin matrix. In some cases, resins may contain latent reactive groups (e.g., protected reactive groups) which must be activated before the dithioamine or dithiane is immobilized. Useful resins for immobilization of dithioamines or dithianes of this invention include among others, aminoalkyl resins, Rink amide resin, MBHA resins, indole resins, hydroxylamine resins, Sieber amide resins, PAL resins, sulfamyl-based resins, Wang resin, HMPA-AM resins, Merrifield resin, PAM resins, oxime resins, various safety-catch resins and the like. One of ordinary skill in the art can employ any such resins to immobilize the dithioamines and dithianes of this invention using well-known methods or routine adaptation of such well-known methods. Albericio, F. and Tulla-Puche (ed) (2008) The Power of Functional Resins in Organic Synthesis (Wiley-Verlag) provided a description of various useful resins and methods of using such resins for immobilization of various chemical species. This reference is incorporated by reference herein in its entirety to illustrate what is known in the art concerning such resins, methods for their use and methods of immobilization that are useful in this invention.

The invention provides specific immobilized reducing agents and immobilized dithianes which are precursors thereof of formulas:

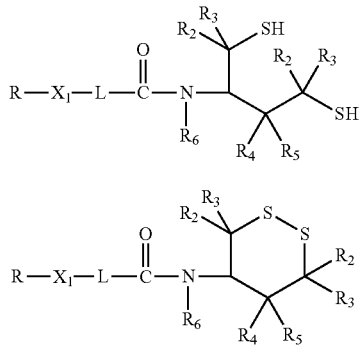

where R is a surface including a resin,
L is a divalent linker as described herein,
$R_2$-$R_6$ are as defined above, and
X1 is a bond, —O—, —OCO—, —COO—, —NHCO—, —CONH—, —SO$_2$—NH—, —SO$_2$—NH—CO—, —NHCONH—, or —OCOO—.

In specific embodiments, $R_2$-$R_6$ are all hydrogens. In specific embodiments, —X1-L- is —NHCO—(CH$_2$)r-, where r is 1-6 and r is preferably 2; or —X1-L- is —NHCO—CH$_2$CH$_2$OCH$_2$CH$_2$—.

In specific embodiments, compounds of this invention of formulas I, IA, IB and II contain a reactive functional group for attachment of the compound to a T species (as described herein, a polymer or a surface. The reactive functional group can, for example, be a group that reacts with an amine, a carbonyl, a carboxylate, a carboxylic ester, sulfamyl group (—SO$_2$—NH$_2$), or hydroxyl group. Generally, sulfhydryl reactive groups are less preferred as care must be taken to protect sulfhydryl groups on the reducing agent. Preferably such reactive groups react to conjugate the species under conditions such that the reducing agent substantially retains functionality and which do not substantially detrimentally affect biological activity of interest of the T species (if any). A variety of reactive groups useful for such coupling are known in the art and one of ordinary skill in the art can select among such known reactive groups to practice the methods of the present invention without undue experimentation.

An overview of bioconjugation methods that can be employed in the present invention is found in Hermanson, G. T. Bioconjugation Techniques (2nd Ed.) 2008 Academic Press/Elsevier London, UK. This reference also contains detailed descriptions of homobifunctional and heterobifunctional crossing linking reagents which can be employed for conjugation.

Amine-reactive groups are exemplified by a carboxylate group, a carboxylate ester group, an acid chloride group, an aldehyde group, an acyl azide group, an epoxide, an isothiocyanate group, an isocyanate group, an imidoester group or an anhydride group. Amines react with carboxylates in the presence of coupling reagents, such as carbodiimides. Amine-reactive groups include active carboxylic acid ester groups, such as succinimidyl ester groups or sulfosuccinimidyl ester groups (e.g., N—OH succinimidyl or N—OH sulfosuccinimidyl groups); haloalkyl ester groups, such as trifluoroalkyl ester groups and hexafluoroalkyl ester groups; halophenyl ester groups, particularly fluorophenyl and chlorophenyl ester groups, including penta- and tetrafluorophenyl ester groups, pentachlorophenyl ester groups; nitrophenyl ester groups, including 2-nitrophenyl, 4-nitrophenyl and 2,4-dinitrophenyl ester groups; as well as other substituted phenyl ester groups, including sulfodichlorophenol ester groups.

General conditions for carrying out reactions between amine-reactive groups and amino groups of an amino acid, peptide or protein are well known in the art and can be carried out by one of ordinary skill in the art without undue experimentation.

Although not preferred, sulfhydryl-reactive groups are exemplified by haloacetyl and haloacetamidyl groups, particularly iodoacetyl and bromoacetyl or corresponding acetamidyl groups, maleimide groups, haloalkyl groups, halobenzyl groups, acryloyl groups, epoxide groups, groups that undergo thiol-disulfide exchange, such as dipyridyl disulfide groups or 2,2'-dihydroxy-6,6'-dinaphthyldisulfide groups, or thiosulfate groups. General conditions for carrying out reactions between sulfhydryl-reactive groups and sulfhydryl groups are well known in the art and can be carried out by one of ordinary skill in the art without undue experimentation.

Carboxylate-reactive functional groups are exemplified by amines (e.g., employing a carbodiimide), hydrazine groups, hydrazide groups, sulfonylhydrazide groups, diazoalkyl groups, sulfamyl, diazoaryl groups, diazoacetyl groups, hydroxyl groups or sulfhydryl groups.

Hydroxyl-reactive functional groups are exemplified by isocyanate groups; epoxide groups; alkyl or aryl halide group, e.g., a halotrityl group; an activated carbamate group, an activated ester group (such as described above), N,N'-disuccinimidyl carbonate groups or N-hydroxysuccinimidyl chloroformate groups. Aldehyde and ketone-reactive groups are exemplified by hydrazine groups and derivatives thereof including hydrazides, semicarbazides and carbohydrazides, and amino groups. Various methods for introduction of aldehyde and ketone groups into amino acids, peptides and proteins are known in the art.

Azide groups react with alkenyl or akynyl groups (in so-called Click reactions) to form triazolines or triazoles. Click reactions can be used to link a reducing agent of the invention with a T group or to a surface. Linkers formed in such reactions will include a triazoline or triazole moiety.

Phosphinothioesters react with azide groups as described in U.S. Pat. Nos. 6,972,320 and 7,256,259, and 7,317,129 and U.S. published application US 2010/0048866 to form amide bonds in a traceless Staudinger ligation. Phosphinothioesters can be prepared employing phosphinothiol reagents as also described in these references. Each of these references is incorporated by reference herein in its entirety for descriptions of such ligation reactions, methods of making azides and methods of making phosphinothioesters.

Aldehyde, ketone, azide activated esters groups, thioester, phosphinothiol groups are introduced by any art-known methods.

Homobifunctional crosslinking reagents contain two identical reactive groups separated by a spacer or linker moiety. Heterobifunctional crosslinking reagents contain two reactive groups with different selectivity for reaction, e.g., an amine-reactive group and a sulfhydryl-reactive group separated by a spacer or linker moiety. Various homobifunctional and heterobifunctional crossing linkage reagents are known in the art and a number are commercially available from Pierce (Thermo Scientific), Rockford, Ill., Sigma-Aldrich, St. Louis, Mo. or Molecular Probes (Life Technologies), Eugene Oreg.

Useful homobifunctional crosslinking reagents include those carrying two amine-reactive groups, those carrying two carboxylate reactive groups, or those carrying two aldehyde or ketone reactive groups. Homobifunctional crosslinking reagents carrying sulfhydryl reactive groups are generally not preferred. Such reagents can be employed if appropriate sulfhydryl group protecting agents, such as acyl groups, are employed to prevent reaction with the sulfhydryl groups of the reducing agent.

Useful heterobifunctional crosslinking reagents include those carrying one of an amine-reactive group, a sulfhydryl reactive group, a carboxylate reactive group, or an aldehyde or ketone reactive group and one of a different reactive group selected from an amine-reactive group, a sulfhydryl reactive group, a carboxylate reactive group, or an aldehyde or ketone reactive group. Again heterobifunctional crosslinking reagents carrying sulfhydryl reactive groups are generally not preferred as noted above.

Homobifunctional and heterobifunctional crosslinking reagents can in general contain any spacer or linking moiety compatible with the reactive groups therein wherein the spacer or linker itself is not reactive with the compounds to be conjugated. In specific embodiments, disulfide moieties are not preferred in such spacers or linkers. In specific embodiments, the spacer or linking moiety typically ranges from 3-20 atoms (typically C, O, S and/or N atoms) in length (including residues from the reactive group), and optionally contain one or more carbon-carbon double bonds, and/or a 5- or 6-member alicyclic, heterocyclic, aryl or heteroaryl ring. Carbon atoms in the spacer or linker are often substituted with one or more hydroxyl groups, oxo moieties (=O), or halogens (e.g., F). Nitrogen groups in the linker may be substituted hydrogen or with C1-C3 alkyl groups. The spacer or linker may contain one or two —$SO_2$— moieties. The spacer or linker may be selectively cleavable by change of conditions (e.g., pH change), addition of a cleavage reagent, or photoirradiation (e.g., UV irradiation). In specific embodiments, a cleavable linker includes a cleavable linker contains a diol moiety which is selectively cleavable by treatment for example with periodate, an ester moiety, which is selectively cleavable by treatment with hydroxylamine, a sulfone moiety (—$SO_2$—) which is selectively cleavable under alkaline conditions.

Homobifunctional crosslinking reagents can be used, for example, to conjugate an amine group of an reducing agent or acylated precursor thereof with an amine functionality on a biological or chemical species T, polymer or a surface. Amine-reactive groups employed in homobifunctional crosslinking reagents include among others, activated ester groups, such as NHS esters (N-hydroxysuccinimide esters) or sulfo NHS esters (N-hydroxysulfosuccinimide esters), imidoester group, such as methylimidate salts, isothiocyanate groups and aryl halide groups, such as difluorobenzene derivatives. Amine-reactive homobifunctional include among others: dithiobis(succinimidylproprionate) [DSP] and its sulfo-NHS analog [DTSSP], disuccinimidyl suberate [DSS] and its sulfo-NHS analog [BS3], disuccinimidyl tartarate [DST] and its sulfo NHS analog [sulfo-DST], bis(2-succinimidyloxy-carbonyloxy)ethylsulfone [BSOCOES] and its sulfo-NHS analog [sulfo-BSOCOES], ethylene glycol bis(succinimidylsuccinate) [EGS] and its sulfo-NHS analog [sulfo-EGS], disuccinimidyl glutarate [DSG], N,N'-disuccinimidyl carbonate [DSC], dimethyl adipimidate [DMA], dimethyl 3,3-dithiobispropionimidate [DTBP], 4,4'-disiothiocyanatostilbene-2,2'-disulfonic acid salts, 1,5-difluoro-2,4-dinitrobenzene [DFDNB], 4,4'-difluoro-3,3'-dinitrodiphenylsulfone.

Hydroxyl-reactive homobifunctional crosslinking reagents can be used to conjugate a hydroxyl group on a reducing agent or acylated precursor thereof with a hydroxyl group substituent on a chemical or biological T species, a polymer or a surface. Hydroxyl-reactive groups include those having epoxide groups, such as diglycidylethers, particularly 1,4-butanediol diglycidyl ether.

A carboxylate group on a reducing agent or acylated precursor thereof can be conjugated to a carboxylate group substituent on a chemical or biological T species, a polymer or a surface, for example, by generating an active ester at the carboxylate groups and esterifying the active esters with an alkanediol crosslinking reagent, such a 1,6-hexane diol, or 1,12-dodecanediol.

Aldehyde/ketone-reactive homobifunctional crosslinking reagents can be used to conjugate an aldehyde or ketone group of a reducing agent or acylated precursor thereof of this invention with an aldehyde or ketone group substituent on a phenylboronate compound. Bis-hydrazide reagents can be used to crosslink molecules containing aldehyde or ketone groups; examples of such crosslinking reagents include among others adipic acid dihydrazide and carbohydrazide.

Heterobifunctional crosslinking reagents include those which contain an amine reactive group and a sulfhydryl-reactive group. For example, such a heterobifunctional crosslinking reagent can be used to link an amine group on a compound of this invention with a sulfhydryl substituent in a T species of this invention.

Exemplary heterobifunctional crosslinking reagents include those carrying an activated ester group, such as an NHS ester (or sulfo-NHS ester) group or a nitrophenyl or other substituted phenyl ester and a maleimide group; those carrying such an activated ester group and a dithiopyridyl group, those carrying an activated ester group and an haloacetyl group (e.g., an iodoacetyl group), or those carrying an imidoester group and a maleimide group.

Exemplary heterobifunctional amine/sulfhydryl-reactive crosslinking reagents include, among others, N-(γ-maleimidobutyryloxy)succinimide ester [GMBS] and its sulfo-NHS analog [sulfo-GMBS], 4-succinimidyloxycarbonyl-α-(2-pyridyldithio)toluene [SMPT], succinimidyl-4-(N-maleimidomethyl)cyclohexane-1-carboxylate [SMCC] and its sulfo-NHS analog [sulfo-SMCC], m-maleimidobenzoyl-N-hydroxy-succinimide ester [MBS] and its sulfo-HNS analog [sulfo-MBS], N-succinimidyl(4-iodoacetyl)-aminobenzoate [SIAB] and its sulfo-HNS analog [sulfo-SIAB], succinimidyl-6-(iodoacetyl)aminohexanoate [SIAX], N-succinimidyl-3-92-pyridylthio)propionate [SPDP], succinimidyl-4-(p-maleimidophenyl)butyrate [SMPB] and its sulfo-NHS analog [sulfo-SMPB], succinimidyl-([N-maleimidopropionamidol]ethyleneglycol esters [SM(PEG)n, where n is 4, 6, 8, 12, 24] and p-nitrophenyl iodoacetate [NPIA], N-hydroxysuccinimidyl 2,3-dibromopropionate [SDBP].

Heterobifunctional crosslinking reagents also include those which contain one of an amine-reactive, carboxylate-reactive or carbonyl-reactive group and a photoreactive group which is activated on irradiation to reactive with various reactive groups, including nucleophiles, reactive hydrogen, active hydrogen amines or olefins.

It will be appreciated that it may be necessary dependent upon the conjugation method employed to acylate or otherwise protect the sulfhydryl groups of the reducing agent or other potentially reactive groups therein from undesired conjugation. Useful thiol protective groups, amine protecting groups and protective groups for various other reactive groups are known in the art, for example as described in Wutts, P. G. and Greene, T. (2007) Green's Protecting Groups in Organic Synthesis (Fourth Edition) John Wiley & Sons, N.Y.

The compounds of formulas I, IA, IB and II can be in the form of salts, for example ammonium ($—NR_6R_7H^+$) salts, with a selected anion or quaternized ammonium salts (e.g., $—NR_6R_7R_{20}^+$, where $R_{20}$ is a C1-C3 alkyl group). The salts can be formed as is known in the art by addition of an acid to the free base. Salts can be formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In specific embodiments, compounds of the invention can contain one or more negatively charged groups (free acids) which may be in the form of salts. Exemplary salts of free acids are formed with inorganic base include, but are not limited to, alkali metal salts (e.g., $Li^+$, $Na^+$, $K^+$), alkaline earth metal salts (e.g., $Ca^{2+}$, $Mg^{2+}$), non-toxic heavy metal salts and ammonium ($NH_4^+$) and substituted ammonium ($N(R')4+$ salts, where R' is hydrogen, alkyl, or substituted alkyl, i.e., including, methyl, ethyl, or hydroxyethyl, specifically, tri methyl ammonium, triethyl ammonium, and triethanol ammonium salts), salts of cationic forms of lysine, arginine, N-ethylpiperidine, piperidine, and the like. Compounds of the invention can also be present in the form of zwitterions. Compound of formulas I, IA, IB and II also include those which are pharmaceutically acceptable salts, which refers to those salts which retain the biological effectiveness and properties of the free bases or free acids, and which are not biologically or otherwise undesirable.

The scope of the invention as described and claimed encompasses the racemic forms of the compounds as well as the individual enantiomers and non-racemic mixtures thereof. The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, enantiomers of the invention exhibit specific rotation that is + (positive). Preferably, the (+) enantiomers are substantially free of the corresponding (−) enantiomer. Thus, an enantiomer substantially free of the corresponding enantiomer refers to a compound which is isolated or separated via separation techniques or prepared free of the corresponding enantiomer. "Substantially free," means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); Wilen, S. H. Tables of Resolving Agents and Optical Resolutions p. 268 (E. L. Eliel, Ed., Univ. of Notre Dame Press, Notre Dame, Ind. 1972).

The invention provides methods for reducing or preventing disulfide bond formation in one or more molecules having one or more sulfhydryl groups which comprise the step of contacting the one or more molecules with one or more compounds of this invention, particularly one or more compounds of formulas I, IA or IB. In a specific embodiment, the methods are carried out under physiological conditions. In a specific embodiment, the methods are carried out at a pH ranging from 6-8. In a specific embodiment, the methods are carried out at a pH ranging from 6.5 to 7.5. In a specific embodiment, the methods are carried out employing one or more compounds of the invention which are covalently attached to a surface. In specific embodiments, the surface is organic or inorganic with specific examples of such surfaces provided herein. In a specific embodiment, the one or more compounds are S-acylated and the acyl groups are removed to activate the one or more compounds as reducing agents. Activation of the S-acylated compounds can occur prior to contacting the one or more molecules carrying sulfhydryl groups. Activation of the S-acylated compounds can occur at about the same time as contacting the one or more molecules carrying sulfhydryl groups. For example, the contacting step and S-acyl group removal can occur in tissue or in a cell which contains one or more esterases which function for removal of the acyl groups.

In a specific embodiment, reducing or preventing disulfide bond formation reduces or prevents the formation of dimers or other oligomers of the one or more molecules having sulfhydryl groups. In a specific embodiment, reducing or preventing disulfide bond formation functions to modulate a biological activity of the one or more molecules having sulfhydryl groups. Modulation of the biological activity includes a reduction in such activity or an enhancement of such activity. In specific embodiments, the one or more molecules carrying sulfhydryl groups are biological molecules, more specifically are biological macromolecules and yet more specifically are peptides, proteins, carbohydrates or nucleic acids.

In a specific embodiment, the molecules having one or more sulfhydryl groups are peptides or proteins and reducing or preventing disulfide bond formation functions to modulate a biological activity of the one or more peptides or proteins. In a specific embodiment, reducing or preventing disulfide bond formation functions to reduce a biological activity of a peptide or protein. In another embodiment, reducing or preventing disulfide bond formation functions to enhance a biological activity of a peptide or protein. In a specific embodiment, the peptide or protein is redox-sensitive peptide or protein, for example a peptide or proteins the biological activity of which is affected by oxidative stress as is described in Cumming et al. [34]. Cumming et al. is incorporated by reference herein for its description of such redox-sensitive peptides and proteins and specific examples given therein.

Of particular interest for therapeutic application of the compounds of this invention are redox-sensitive peptides and proteins whose function is associated with human or animal disease. Non-limiting specific examples of such redox-sensitive peptides or proteins include PTEN (human phosphatase PTEN), SOD (superoxide dismutase), and pMK2 (an isoform of pyruvate kinase). Decreased PTEN activity is associated with many cancers (i.e., PTEN activity is associated with cancer protection). A cysteine residue near the active site of human phosphatase PTEN is known to be sensitive to oxidation, such that its activity is decreases. Prevention of this inactivation employing a reducing agent or precursor thereof of this invention can be of therapeutic benefit. Superoxide dismutase (Cu/Zn SOD) can be inactivated by the formation of disulfide-linked dimers. Decreased SOD activity is believed to be a cause of amylotropic lateral sclerosis (ALS) (35, 36). Prevention of decreased SOD activity employing a reducing agent or precursor thereof of this invention can be of therapeutic benefit.

In specific embodiments herein, the dithioamine reducing agent, dithiane precursor or acylated precursor thereof is conjugated to a biological or chemical species which targets or directs the conjugated reducing agent to a specific redox-sensitive peptide or protein. The biological or chemical species is for example a ligand, a substrate or a pharmacophore of the target peptide or protein (which may be an enzyme).

PTEN is believed to function by attack/removal of a phosphoryl group from C3 of the inositide below by a cysteine residue. This inositide is the product of PTEN catalysis:

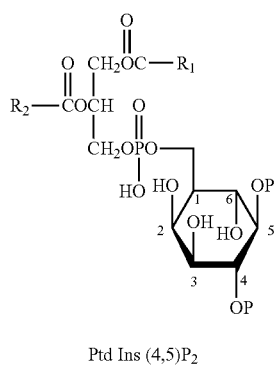

Ptd Ins (4,5)P$_2$

The PTEN cysteine can form a disulfide bond with another cysteine residue inactivating PTEN. This inositide represents a pharmacophore of PTEN and is highly anionic. To target a reducing agent or acylated precursor thereof to PTEN, a highly anionic chemical species can be used which provides a substantial pharmacological equivalent of the phosphoinositol moiety.

A specific example of such a highly anionic chemical species is 1,3,5-tricarboxybenzene. In an exemplary embodiment hereof one or more reducing agents, dithianes or acylated precursors thereof are conjugated to T which is 1,3,5-tricarboxybenzene (or a salt thereof), via one of the carboxyl groups therein:

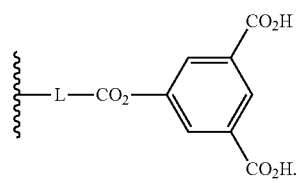

In another exemplary embodiment hereof one or more reducing agents or acylated precursors thereof are conjugated to T which is a 1,3,5-tricarboxybenzyl group (or a salt thereof), via a spacer or linker group:

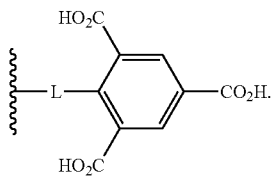

Conjugates of tricarboxybenzene with one or more of the reducing agents of formulas I, IA or IB can be prepared by methods that are well-known in the art, for example by methods that are described in Hermanson, G. T. (2008) Bioconjugate Techniques (Second Edition) Academic Press, N.Y., for example Part I, Chapters 1 and 2. More specifically, a suitable reactive group can be installed on the 1,3,5-tricarboxybenzene and the functionalized T group can then be conjugated to a reducing agent or acylated precursor herein which carries an appropriate reactive group (as described herein above) employing an art-known homo- or heterobifunctional crosslinking reagent as described for example in Hermanson, G. T. (2008) Bioconjugate Techniques (Second Edition) Academic Press, N.Y., Chapters 4 and 5.

More generally the invention provides dithioamine reducing agents, dithiane precursors or S-acyl precursors thereof which are targeted to a cationic site for example which contain a pharmacophore of the phosphoinositol moiety. The invention provides compounds of formulas V and VI:

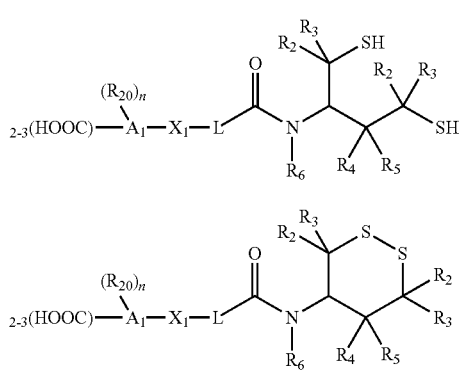

and salts thereof,
where $R_2$-$R_6$ are as defined for formula I above,
L is an optional divalent linker as defined above,
A1 is an n-valent di- or tricarboxylic acid species which is selected from an aliphatic group, a heterocyclic group, an aryl group, or a heteroaryl group;
$R_{20}$ is hydrogen, an alkyl group having 1-3 carbon atoms, an aryl group, an arylalkyl group, wherein the alkyl, aryl or aryalkyl group is optionally substituted with one or more halogens, and
X1 is a bond, —O—, —CO—, —OCO—, —NHCO—, —COO—, or —CO—NH—.

In specific embodiments, A1 is a cycloalkyl or cycloalkenyl group having 4-10 carbon atoms. In specific embodiments, A1 is an alkyl group having 5-8 carbon atoms, a phenyl group, a benzyl group, a cyclohexyl group, a cyclohexenyl group, a cyclopentyl group, a cyclobutyl group, a furan, a tetrahydrofuran or a tetrahydropyran. In specific embodiments, the A1 group carries three carboxylic acid groups. In specific embodiments, X1 is a bond. In specific embodiments L is —$(CH_2)_q$—, where q is 0, 1, 2, 3, 4, 5, or 6. In specific embodiments, $R_2$-$R_6$ are all hydrogens. In specific embodiments, any $R_{20}$ are hydrogens or alkyl groups having 1-3 carbon atoms.

In specific embodiments, A1 is a tricarboxylic acid species selected from:

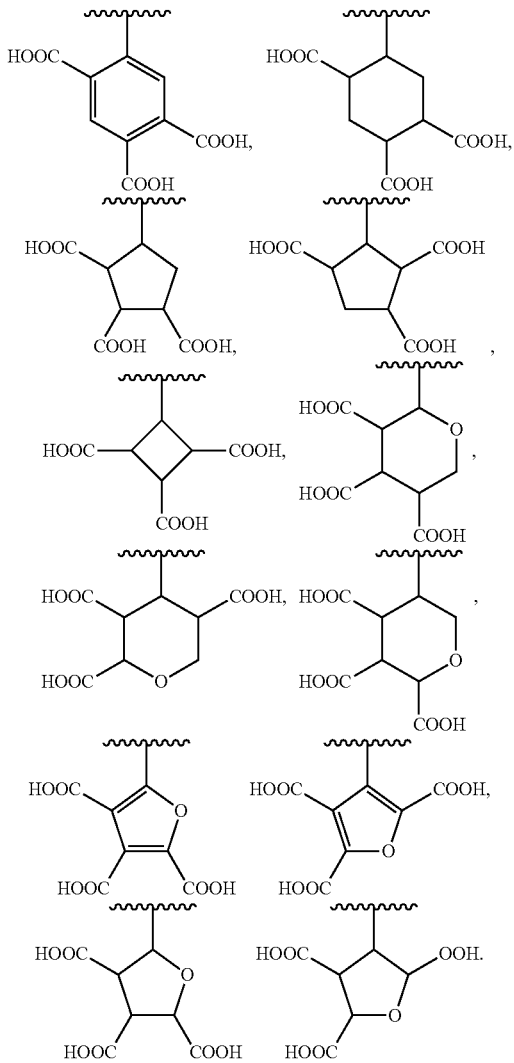

The carboxylic acid substituted A1 group may be a mixture of regioisomers.

Reducing agents and acylated precursors thereof of formulas I, IA, and IB are useful as research reagents for reducing disulfide bonds and other redox applications, particularly in applications directed to biological molecules, such as peptide, proteins, carbohydrates and nucleic acids. In various applications, reducing agents of this invention can be added to biological buffers. Compounds of formulas II represent the oxidized form of the reducing agents of formulas I, IA and IB (noting that the specific chiral forms corresponding to formulas IA and IB are not specifically shown). These oxidized forms are also useful as research reagents, for example, a combination of reduced and oxidized compounds of formulas I and II in appropriate ratio in solution (e.g., aqueous solution) can provide a redox buffer with a selected reduction potential. Redox buffers can be employed for example for refolding of proteins.

One or ordinary skill in the art will recognize additional applications for the reducing agents and acylated precursors thereof. For example, reducing agents are employed for treating hair, e.g. for removal of hair coloring and the like.

The term kit refers to kits including one or more of the reducing agents, or acylated precursors thereof or dithianes precursors thereof which are useful for preventing or inhibiting the formation of disulfide bonds or for cleaving disulfide bonds. In one embodiment, kits of this invention include one or more of the compounds of the present invention or mixtures thereof and optionally reagents for ligating, or conjugating such compounds with a biological or chemical species as discussed herein. The kits optionally include one or more solvents or buffers for application of a reducing agent of this invention. In another embodiment, kits of this invention include one or more compounds of this invention of this invention and optionally reagents, such as one or more homo- or heterobifunctional crosslinking reagents, for ligating or conjugating to a surface. The kit may also include one or more surfaces, for example, in the form of plates, sheets, beads, particles, microspheres, microparticles, nanoparticles or the like to which a compound of this invention is to be immobilized or conjugated. A kit may also include a reagent for removing S-acyl groups of S-acyl precursors of the reducing agents herein, such as hydroxylamine or an esterase.

Kits of the invention may comprise a carrier being compartmentalized to receive in close confinement one or more containers, such as vials, test tubes, ampules, bottles and the like. Each of such container means comprises components or a mixture of components as described above (reducing agents, precursors, solvents or buffers, other reagents, etc.) The kits of the invention may further comprise one or more additional components (e.g., reagents and/or compounds) necessary or desirable for carrying out one or more particular applications of the compositions of the present invention. In general kits may also contain one or more buffers, control samples, carriers or recipients, vessels for carrying out one or more reactions, one or more additional compositions of the invention, one or more sets of instructions, and the like. IN specific embodiments of kits herein the reducing agent is DTBA or a salt thereof.

The invention is also directed to art-known kits in which DTT therein is replaced with one or more reducing agents of this invention and particularly with DTBA or a salt thereof. Such its include DNA ligation or DNA blunting kits where DTT in buffers therein is replaced with one or more reducing agents of this invention, particularly DTBA or a salt thereof. Kits of this invention also include kits for protein purification or protein assay kits which are compatible with reducing agents.

An aliphatic group as used herein refers to a monovalent non-aromatic hydrocarbon group which include straight chain, branched, or cyclic hydrocarbon groups which can be saturated or unsaturated with one or more double bonds or one or more triple bonds. Aliphatic groups may contain portions which are straight-chain or branched in combination with one or more carbon rings. Carbon rings of aliphatic groups may contain one or more double bonds or one or more triple bonds. Carbon rings of aliphatic groups can contain 3- to 10-membered rings. Such carbon rings may be fused and may be bicyclic or tricyclic. Aliphatic groups are optionally substituted with one or more non-hydrogen substituents where optional substituents are described herein. Unless otherwise specified, an aliphatic group can contain 1-20 carbon atoms or can contain 1-10 carbon atoms. Aliphatic groups include those containing 1-3, 1-6, and 1-8 carbon atoms. Aliphatic groups include, among others, alicyclic groups, alkyl groups, alkenyl groups and alkynyl groups.

An alicyclic group as used herein refers to a monovalent non-aromatic cyclic hydrocarbon group which can be saturated or unsaturated with one or more double bonds or one or more triple bonds. Alicyclic rings include those containing 3- to 10-membered carbon rings. Alicyclic groups include those containing one, two, three or more rings which may be fused or linked by straight chain or branched alkylene, alkenylene or alkynylene moieties. Alicyclic groups include bicyclic and tricyclic rings. Alicyclic groups include those in which one or more carbon rings are substituted with a straight-chain or branched alkyl, alkenyl or alkynyl group. To satisfy valence requirements, a ring atom may be substituted with hydrogen or optionally with non-hydrogen substituents as described herein. One or more carbons in an alicyclic group can be —CO— groups, i.e. a carbon can be substituted with an oxo (=O) moiety. Alicyclic groups are optionally substituted with one or more non-hydrogen substituents where optional substituents are described herein. Unless otherwise specified, an alicyclic group can contain 3-20 carbon atoms or can contain 3-12 carbon atoms. Alicyclic groups include those containing 3-6 and 3-8 carbon atoms. Alicyclic groups include among others cycloalkyl, cycloalkenyl, cyclopropyl, cyclobutyl, cyclopentyl, cyclopentadienyl, cyclohexyl, cyclohexenyl and cyclohexadienyl groups, all of which are optionally substituted.

A heterocyclic group as used herein refers to a monovalent non-aromatic cyclic hydrocarbon group wherein one or more of the rings contain one or more heteroatoms (e.g., N, S, O, or P) which rings can be saturated or unsaturated with one or more double bonds or one or more triple bonds. In specific embodiments of this invention, heterocyclic rings which are substituents of the compounds of formulas IA and IB do not contain boron atoms. Heterocyclic rings include those containing 3- to 10-membered rings where 1, 2 or 3 of the ring members are heteroatoms. Heterocyclic groups include those containing one, two, three or more rings which may be fused or linked by straight chain or branched alkylene, alkenylene or alkynylene moieties. Heterocyclic groups include bicyclic and tricyclic groups. Heterocyclic groups include those in which a heterocyclic ring is substituted with a straight-chain or branched alkyl, alkenyl or alkynyl group. To satisfy valence requirements, a ring atom may be substituted with hydrogen or optionally with non-hydrogen substituents as described herein. One or more carbons in a heterocyclic group can be —CO— groups. One or more carbons in a heterocyclic ring can be —CO-groups. Heterocyclic groups are optionally substituted with one or more non-hydrogen substituents where optional substituents are described herein. Ring carbons and, where chemically feasible, ring heteroatoms are optionally substituted. Unless otherwise specified, a heterocyclic group can contain 3-20 carbon atoms, can contain 3-12 carbon atoms or can contain 3-6 carbon atoms. Heterocyclic groups include those containing one or two 4-, 5- or 6-member rings at least one of which has one, two or three N, O or S atoms and wherein a ring optionally has one or two double bonds. Heterocyclic groups include those containing a single 5- or 6-member ring having one, two or three N, O or S atoms and optionally having one or two double bonds. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic groups include those having 5- or 6-member rings and two different heteroatom, e.g., N and O, O and S or N and S. Heterocyclic groups include those having 5- or 6-member rings and a single heteroatom, e.g., N S or O. Specific heterocyclic groups include among others among others, pyrrolidinyl, piperidyl, piperazinyl, pyrrolyl, pyrrolinyl, furyl, tetrahydropyranyl, tetrahydrofuryl, thienyl, morpholinyl, oxazolyl, oxazolinyl, oxazolidinyl, indolyl, triazoly, and triazinyl groups, all of which are optionally substituted.

Aryl groups are monovalent groups containing at least one aromatic ring. Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups may contain one or more non-aromatic alicyclic rings in addition to an aromatic ring. Aryl groups are optionally substituted with one or more non-hydrogen substituents as described herein. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Unless otherwise specified, an aryl group can contain 5-20 carbon atoms or can contain 6-14 carbon atoms. Aryl groups also include those containing 6-12 carbon atoms.

Heteroaryl groups are monovalent groups having one or more aromatic rings in which at least one ring contains a heteroatom (a non-carbon ring atom). Heteroaryl groups include those having one or two heteroaromatic rings carrying 1, 2 or 3 heteroatoms and optionally having one 6-member aromatic ring. Heteroaryl groups can contain 5-20, 5-12 or 5-10 ring atoms. Heteroaryl groups include those having at least one aromatic ring containing a heteroatom and one or two alicyclic, heterocyclic or aryl ring groups. Heteroaryl groups include those having one aromatic ring containing a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include pyridinyl, pyrazinyl, pyrimidinyl, quinolinyl, and purinyl groups.

Alkyl groups are monovalent groups and include straight-chain, branched and cyclic alkyl groups. Unless otherwise indicated alkyl groups include those having from 1 to 20 carbon atoms. Alkyl groups include alkyl groups having 1 to 3 carbon atoms, alkyl groups having from 4-7 carbon atoms and alkyl groups having 8 or more carbon atoms. Cyclic alkyl groups include those having one or more rings. Cyclic alkyl groups include those which have 1, 2 or 3 rings. Cyclic alkyl groups also include those having 3-10 carbon atoms. Cyclic alkyl groups include those having a 3-, 4-, 5-, 6-, 7-, 8-, 9- or 10-member carbon ring and particularly those having a 3-, 4-, 5-, 6-, 7-, or 8-member ring. The carbon rings in cyclic alkyl groups can also carry straight-chain or branched alkyl group substituents. Cyclic alkyl groups can include bicyclic and tricyclic alkyl groups. Alkyl groups are optionally substituted with one or more non-hydrogen substituents as described herein. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, cyclohexyl, decalinyl, and norbornyl, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups. Substituted alkyl group include alkyl group substituted with one or more hydroxyl groups. Substituted alkyl groups include groups substituted with two or more hydroxyl groups, particularly where two hydroxyl groups are substituted on adjacent carbon atoms.

Arylalkyl groups are monovalent alkyl groups substituted with one or more aryl groups wherein the alkyl groups optionally carry additional substituents and the aryl groups are optionally substituted. Specific arylakyl groups are phenyl-substituted alkyl groups, e.g., benzyl groups or phenethyl groups which are optionally substituted. Heteroarylalkyl groups are monovalent alkyl groups substituted with one or more heteroaryl groups wherein the alkyl groups optionally carry additional substituents and the aryl groups are optionally substituted. Alkylaryl groups are monovalent aryl groups substituted with one or more alkyl groups wherein the alkyl groups optionally carry additional substituents and the aryl groups are further optionally substituted. Specific alkylaryl groups are alkyl-substituted phenyl groups such as o-, m- or p-tolyl groups which are optionally substituted. Alkylheteroaryl groups are monovalent alkyl groups substituted with one or more heteroaryl groups wherein the alkyl groups optionally carry additional substituents and the heteroaryl groups are optionally substituted.

Alkenyl groups include monovalent straight-chain, branched and cyclic alkenyl groups which contain one or more carbon-carbon double bonds. Unless otherwise indicated alkenyl groups include those having from 2 to 20 carbon atoms. Alkenyl groups include those having 2 to 4 carbon atoms and those having from 5-8 carbon atoms. Cyclic alkenyl groups include those having one or more rings wherein at least one ring contains a double bond. Cyclic alkenyl groups include those which have 1, 2 or 3 rings wherein at least one ring contains a double bond. Cyclic alkenyl groups also include those having 3-10 carbon atoms. Cyclic alkenyl groups include those having a 5-, 6-, 7-, 8-, 9- or 10-member carbon ring and particularly those having a 5- or 6-member ring. The carbon rings in cyclic alkenyl groups can also carry straight-chain or branched alkyl or alkenyl group substituents. Cyclic alkenyl groups can include bicyclic and tricyclic alkyl groups wherein at least one ring contains a double bond. Alkenyl groups are optionally substituted with one or more non-hydrogen substituents as described herein. Specific alkenyl groups include ethylene, propenyl, cyclopropenyl, butenyl, cyclobutenyl, pentenyl, pentadienyl, cyclopentenyl, cyclopentadienyl, hexylenyl, hexadienyl, cyclohexenyl, cyclohexadienyl, including all isomers thereof and all of which are optionally substituted. Substituted alkenyl groups include fully halogenated or semihalogenated alkenyl groups.

Alkynyl groups include mono-valent straight-chain, branched and cyclic alkynyl group which contain one or more carbon-carbon triple bonds. Unless otherwise indicated alkynyl groups include those having from 2 to 20 carbon atoms. Alkynyl groups include those having 2 to 4 carbon atoms and those having from 5-8 carbon atoms. Cyclic alkynyl groups include those having one or more rings wherein at least one ring contains a triple bond. Cyclic alkynyl groups include those which have 1, 2 or 3 rings wherein at least one ring contains a triple bond. Cyclic alkynyl groups also include those having 3-10 carbon atoms. Cyclic alkynyl groups include those having a 5-, 6-, 7-, 8-, 9- or 10-member carbon ring and particularly those having a 5- or 6-member ring. The carbon rings in cyclic alkynyl groups can also carry straight-chain or branched alkyl, alkenyl or alkynyl group substituents. Cyclic alkynyl groups can include bicyclic and tricyclic alkyl groups wherein at least one ring contains a triple bond. Alkynyl groups are optionally substituted with one or more non-hydrogen substituents as described herein.

An alkoxy group is an alkyl group (including cycloalkyl), as broadly discussed above, linked to oxygen, a monovalent —O-alkyl group. An aryloxy group is an aryl group, as discussed above, linked to an oxygen, a monovalent —O-aryl. A heteroaryloxy group is a heteroaryl group as discussed above linked to an oxygen, a monovalent —O-heteroaryl. Alkenoxy, alkynoxy, alicycloxy, heterocycloxy groups are analogously defined. All of such groups are optionally substituted.

As to any of the chemical groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The dithioamines of this invention as illustrated in formulas I, IA and IB can be prepared in view of the descriptions herein, what is known in the art or by routine adaptation of art-known methods from starting materials and reagents which are commercially available or which can be prepared by methods that known in the art or routine adaptation of such methods. Kessler et al. (1994) [10a] and Servent et al. [10b] provide additional methods for the synthesis of synthetic intermediates useful for preparation of the dithioamines of this invention.

DTBA was prepared via the two routes depicted in Scheme 1. A five-step route commenced with the esterification of the amino acid and protection of its amino group. Reduction with lithium aluminum hydride yielded a diol, which was subjected to Mitsunobu conditions to install the requisite sulfur functionality. [11] Deprotection gave DTBA as its HCl salt in 99% purity and an overall yield of 60%. A six-step route that avoids generation of triphenylphosphine oxide, a recalcitrant byproduct of the Mitsunobu reaction [11] provided DTBA.HCl in an overall yield of 56%. In both routes, the product of every step is a white solid.

In a specific embodiment, dithioamines of this invention of formulas I, IA and IB in which $R_1$-$R_3$ and $R_5$ are hydrogens can be prepared employing methods specifically described herein or routine adaptation of such methods employing 3-substitued derivatives of L-aspartic acid, D-aspartic acid, racemic aspartic acid and esters or amine-protected derivatives thereof.

In an embodiment, the invention provides methods for synthesis of 2-amino 1,4-dimercaptobutane and derivatives thereof of formulas I, IA and IB from aspartic acid and derivatives thereof as illustrated in Scheme 1. An amino-protected diester of aspartic acid (e.g., compound 2) is reduced, for example with $LiAlH_4$, to the corresponding diol (e.g., compound 3). The diol is then treated under Mitsunobu conditions with thioacetic acid nucleophile in the presence of an azodicarboxylate reagent, e.g., diisopropyl azodicarboxylate, or diethyl azodicarboxylate and trisubstituted phosphine, e.g., triphenylphospine, or tri(n-butyl)phosphine to form an acetylated dithiol (e.g., compound 4). This reaction is carried out between room temperature and 0° C., preferably at 0° C., in anhydrous THF (polar aprotic solvent). Alternatively, dioxane or dichloromethane (DCM) can also be employed. The acetylated dithiol (e.g., compound 4) is then deacetylated and deprotected (if desired) to the dithiol amine (e.g., DTBA hydrochloride 5). The use of the phosphine can be avoided by reaction of the diol with a sulfonyl chloride reagent, e.g., methanesulfonyl chloride or toluenesulfonyl chloride, to form a disulfonate ester (e.g., compound 6). Thioacetate ($CH_3CO$—SH) is then used to displace the sulfonate in the presence of crown ether in polar aprotic solvent (e.g., DMF) and form the acetylated dithiol (e.g., compound 4), which in turn can be deacetylated to form the dithioamine (e.g., compound 5). These methods can also be used to form S-acyl derivatives of formulas I, IA and IB where $R_8$ is other than hydrogen by choice of thiocarboxylate ($R_8CO$—SH).

Scheme 1

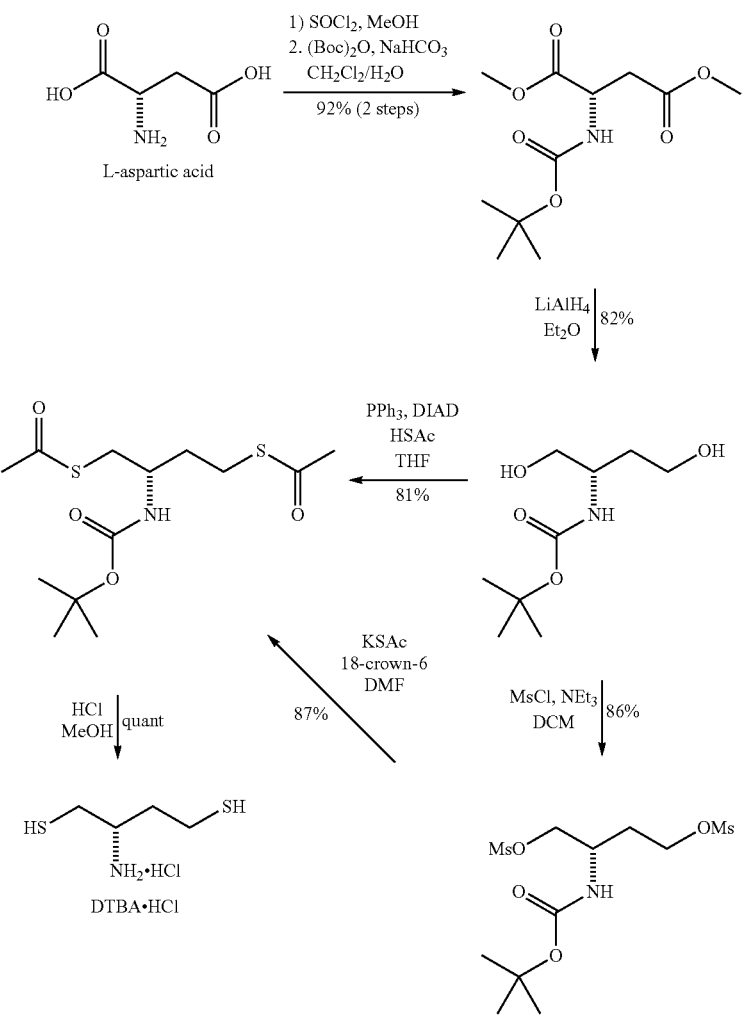

DTBA has desirable physicochemical attributes. Its HCl salt is a nearly odorless white solid with high solubility in water. Using a pH-titration monitored by ultraviolet spectroscopy, [15] we determined the thiol pKa values of DTBA be 8.2±0.2 and 9.3±0.1 (FIG. 3; Table 1) [16] These values are approximately 1 unit lower than those of DTT. This difference is comparable to that between cysteamine and (WE, and likely results from the strong Coulombic and inductive effects of the protonated amino group. By equilibrating reduced DTBA with oxidized DTT and using HPLC to quantify reduced and oxidized species, we found the reduction potential of oxidized DTBA to be $E°'=(-0.317±0.002)$ V (FIG. 4; Table 1). This $E°'$ value is slightly less than that of DTT, consistent with more acidic thiols forming less stable disulfide bonds [17] and with the preorganization of DTT for disulfide-bond formation by its hydroxyl groups, which can form an intramolecular hydrogen bond and manifest a gauche effect.

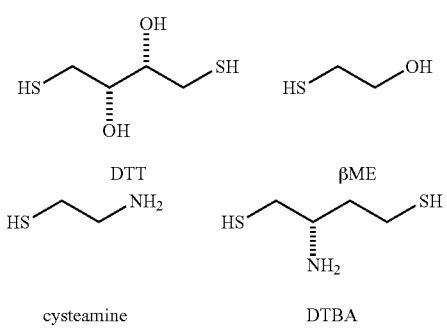

TABLE 1

Physical properties of disulfide-reducing agents.

| | Thiol p$K_a$ | Disulfide Reduction Potential ($E°'$) |
|---|---|---|
| βME | 9.61[a] | −0.260 V[b] |
| Cysteamine | 8.37[c] | −0.203 V[b] |
| DTT (racemate) | 9.2 (10.1)[d] | −0.327 V[e] |

TABLE 1-continued

Physical properties of disulfide-reducing agents.

| | Thiol p$K_a$ | Disulfide Reduction Potential ($E^{o\prime}$) |
|---|---|---|
| DTBA | 8.2 ± 0.2 (9.3 ± 0.1)[f] | (−0.317 ± 0.002) V[f] |

[a]Value is from ref. 12.
[b]Values are from ref. 3f.
[c]Values are from ref. 13.
[d]Values are from ref. 3a.
[e]Value is from ref. 14.
[f]Values are the mean ± SE from this work.

Figure 1B:
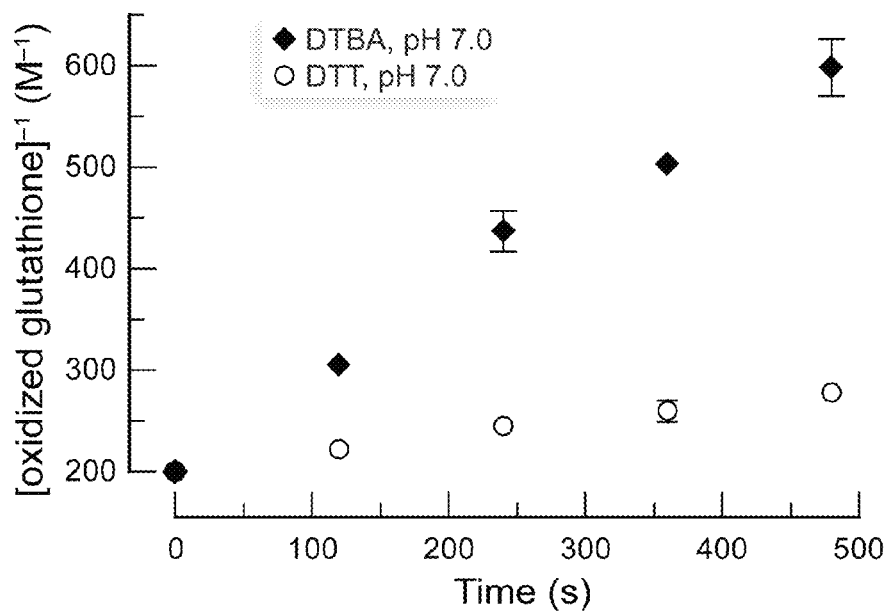
FIG. 1B shows reduction of oxidized l-glutathione; $k_{obs}^{DTBA}/k_{obs}^{DTT}=5.2$ at pH 7.0.

DTBA is an efficacious reducing agent for disulfide bonds in small molecules. We found that DTBA reduces the disulfide bond in oxidized βME 3.5-fold faster than does DTT at pH 7.0, and 4.4-fold faster at pH 5.5 (FIG. 1A). These rate accelerations are commensurate with the lower thiol pKa of DTBA. At pH 7.0, DTBA reduces oxidized L-glutathione 5.2-fold more rapidly than does DTT (FIG. 1B). As oxidized L-glutathione has a net charge of −2 near neutral pH, a favorable Coulombic interaction could contribute to this higher rate acceleration.

Figure 2A:
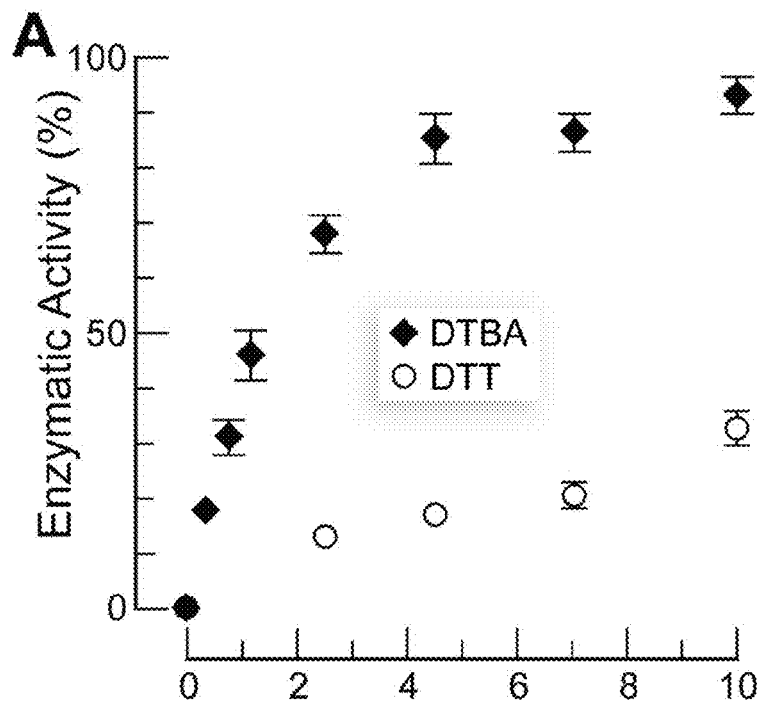
FIGS. 2A and B are grpahs showing the time-course for the reduction of a mixed disulfide in exemplary enzymic active sites by DTBA and DTT in 0.10 M imidazole-HCl buffer, pH 7.0, containing EDTA (2 mM).
Figure 2B:
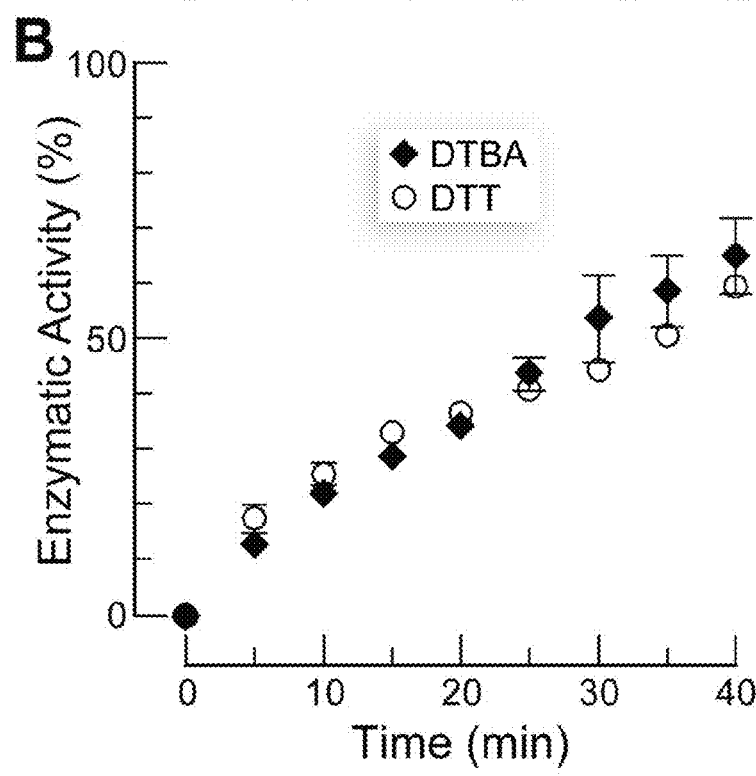
FIG. 2B shows reduction of creatine kinase-Cys283-S—S—l-glutathione; $k_{obs}^{DTBA}/k_{obs}^{DTT}=1.1$.

DTBA is also an efficacious reducing agent for disulfide bonds in proteins. A cysteine residue resides within the active site of papain (Cys25) and near that of creatine kinase (Cys283). Forming a mixed disulfide with that cysteine residue is known to eliminate their enzymatic activities.[2c,18] These two enzymes differ, however, in the electrostatic environment of their active sites. The active site of papain is hydrophobic like its substrates, though there is an anionic region nearby (FIG. 2A).[19] In contrast, the active site of creatine kinase is cationic, complementary to its anionic substrates (FIG. 2B).[20, 21a-c] DTBA reduces a disulfide bond in the hydrophobic/anionic active site of papain 14-fold faster than does DTT (FIG. 2A). In contrast, the two reagents reduce a disulfide bond near the cationic active site of creatine kinase at a similar rate.

The amino group of DTBA confers additional benefits. For example, a disulfide-reducing agent that can be readily isolated, regenerated, and reused incurs less cost and generates less waste.[22] Moreover, extraneous disulfide bonds absorb light at 280 nm, which can confound standard measurements of protein concentration. [23] We reasoned that DTBA could be isolated by its adsorption to a cation-exchange resin. Indeed, >99% of DTBA (but <1% of DTT) was removed from sodium phosphate buffer, pH 8.0, upon addition of Dowex® 50 resin (see: The Examples). We also note that the amino group of DTBA enables its covalent attachment to a soluble molecule, resin, or surface by simple reactions, such as reductive amination (which preserves the cationic charge) or N-acylation. We conclude that the attributes of DTBA enable it to supplant DTT as the preferred reagent for reducing disulfide bonds in biomolecules.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Compounds of the invention, and salts thereof, may exist in their tautomeric form, in which hydrogen atoms are transposed to other parts of the molecules and the chemical bonds between the atoms of the molecules are consequently rearranged. It should be understood that all tautomeric forms, that may exist, are included within the invention.

Every formulation or combination of components described or exemplified herein can be used to practice the invention, unless otherwise stated.

Whenever a range is given in the specification, for example, a temperature range, a pH range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of. Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

THE EXAMPLES

Example 1

Materials and Methods

Commercial reagents were used without further purification. Dithiothreitol (DTT) was from Research Products International (Mt. Prospect, Ill.). Bis(2-mercaptoethyl)sulfone (BMS) was from Santa Cruz Biotechnology (Santa Cruz, Calif.). Papain (lyophilized powder from papaya latex), creatine kinase (lyophilized powder from rabbit muscle), hexokinase (lyophilized powder from Saccharomyces cerevisiae), glucose-6-phosphate dehydrogenase (ammonium sulfate suspension from baker's yeast), $N_\alpha$-benzoyl-L-arginine-4-nitroanilide hydrochloride, (S)-methyl methanethiosulfonate (Kenyon's reagent), trans-4,5-dihydroxy-1,2-dithiane (oxidized DTT), oxidized L-glutathione, oxidized 2-mercaptoethanol, and DOWEX 50WX4-400 ion-exchange resin were from Sigma Chemical (St. Louis, Mo.). Bis(2-mercaptoethyl) sulfone disulfide (oxidized BMS) was synthesized as reported previously [2g]

All glassware was oven or flame-dried, and reactions were performed under $N_2(g)$ unless stated otherwise. Dichloromethane (DCM), diethyl ether, and tetrahydrofuran (THF) were dried over a column of alumina. Dimethylformamide (DMF) and triethylamine were dried over a column of alumina and purified further by passage through an isocyanate scrubbing column. Flash chromatography was performed with columns of 40-63 Å silica, 230-400 mesh (Silicycle, Québec City, Canada). Thin-layer chromatography (TLC) was performed on plates of EMD 250-μm silica 60-$F_{254}$. The term "concentrated under reduced pressure" refers to the removal of solvents and other volatile materials using a rotary evaporator at water aspirator pressure (<20 torr) while maintaining the water-bath temperature below 40° C. Residual solvent was removed from samples at high vacuum (<0.1 torr). The term "high vacuum" refers to vacuum achieved by a mechanical belt-drive oil pump.

$^1$H NMR spectra were acquired at ambient temperature with a Bruker DMX-400 Avance spectrometer at the National Magnetic Resonance Facility at Madison (NMRFAM) and referenced to TMS or residual protic solvent. $^{13}$C NMR spectra were acquired with a Varian MercuryPlus 300 and referenced to residual protic solvent. Electrospray ionization (ESI) mass spectrometry was performed with a Micromass LCT at the Mass Spectrometry Facility in the Department of Chemistry at the University of Wisconsin-Madison. Ellman's assay for sulfhydryl groups was performed with a Varian Cary 50 Bio UV-Vis spectrophotometer. UV absorbance spectra of oxidized DTBA and oxidized DTT were acquired with a Varian Cary 300 Bio UV-Vis spectrophotometer. Thiol $pK_a$ values were determined by using a Varian Cary 50 Bio UV-Vis spectrophotometer. Equilibrium, reduction potential, and kinetic studies on peptides and small molecules were performed on an analytical HPLC (Waters system equipped with a Waters 996 photodiode array detector, Empower 2 software and a Varian C18 reverse phase column). Kinetic studies on proteins were carried out using a Varian Cary 300 Bio UV-Vis spectrometer with a Cary temperature controller.

Example 2

Synthesis of DTBA

A.

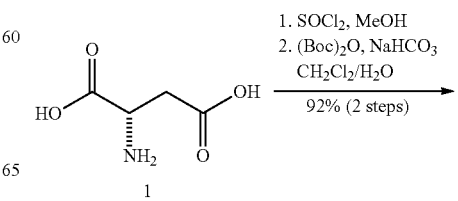

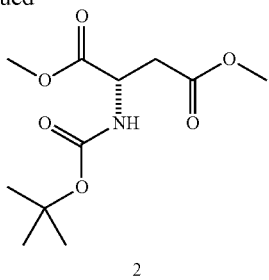

2

L-Aspartic acid (1; 5.002 g, 37.58 mmol) was added to an oven-dried round-bottom flask and placed under an atmosphere of dry N₂(g). The starting material was then dissolved partially with 60 mL of anhydrous methanol, and the mixture was cooled to 0° C. Once the desired temperature was reached, thionyl chloride (8.2 mL, 110 mmol) was added drop-wise. After the addition was complete, the reaction mixture became homogenous, and was warmed slowly to room temperature and left to stir for 14 h. The reaction mixture was then concentrated under reduced pressure, and the resulting diester was dissolved in 150 mL of DCM and 100 mL of water. To this biphasic solution was added sodium bicarbonate (4.212 g, 50.14 mmol) and di-t-butyl dicarbonate (9.841 g, 45.09 mmol), and the reaction mixture was heated at reflux for 4 h. After the reaction was confirmed to be complete by TLC, the reaction mixture was allowed to cool to room temperature. The organic layer was separated, and the aqueous layer was extracted three times with 150 mL of DCM. The organic extracts were combined, washed with 250 mL of saturated NaCl(aq), dried over MgSO₄(s), and concentrated under reduced pressure. Flash chromatography (35% v/v ethyl acetate in hexanes) was used to isolate 2 [(S)-dimethyl 2-(tert-butoxycarbonylamino)succinate] as a white solid (9.080 g, 92%, 2 steps).

¹H NMR (400 MHz, CDCl₃) δ=5.49 (d, J=8.3 Hz, 1H), 4.60-4.57 (m, 1H), 3.76 (s, 3H), 3.70 (s, 3H), 3.01 (dd, J=17, 4.4 Hz, 1H), 2.83 (dd, J=17.0, 4.7), 1.45 (s, 9H); ¹³C NMR (75 MHz, CDCl₃) δ=171.6, 171.5, 155.5, 80.3, 52.8, 52.1, 50.0, 36.8, 28.4; HRMS (ESI) calculated for [C₁₁H₁₉NO₆Na]⁺ (M+Na⁺) requires ink=284.1105, found 284.1113.

B.

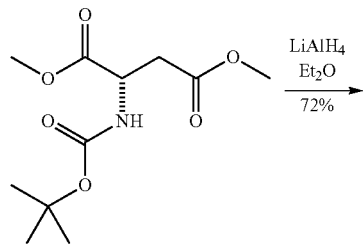

An oven-dried round-bottom flask was charged with lithium aluminum hydride (0.870 g, 22.9 mmol) and placed under an atmosphere of dry N₂(g). The flask was cooled to 0° C. in an ice bath, and 100 mL of anhydrous diethyl ether was added. In a separate dry round-bottom flask, compound 2 (2.021 g, 7.735 mmol) was dissolved in 50 mL of anhydrous diethyl ether. Sonication was required to make the solution completely homogenous. The ester was then added drop-wise to the reaction mixture. Once the addition was complete, the reaction mixture was stirred at 0° C. for an additional 30 min, warmed to room temperature, and allowed to react for an additional 2 h. Subsequently, the reaction mixture was quenched at 0° C. by the slow, sequential addition of 0.87 mL of water, 0.87 mL of 15% w/w NaOH, and 2.6 mL of water. The mixture was left to stir at room temperature for 1 h. The aluminum salts were collected by vacuum filtration, and subjected to continuous solid-liquid extractions with dichloromethane using a Soxhlet apparatus. The organic extracts and the original organic filtrate were combined and concentrated under reduced pressure. Flash chromatography (ethyl acetate) was used to isolate 3 [(S)-tert-butyl 1,4-dihydroxybutan-2-ylcarbamate] as a white solid (1.310 g, 82%). Compound 3 has been prepared from L-aspartic acid by a different route. [10a]

¹H NMR (400 MHz, DMSO-d₆) δ=6.46 (d, J=8.8 Hz, 1H), 4.56 (t, J=5.7 Hz, 1H), 4.34 (t, J=5.1 Hz, 1H), 3.46-3.37 (m, 3H), 3.32 (dt, J=10.6, 5.4 Hz, 1H), 3.23 (dt, J=10.6, 5.9 Hz, 1H), 1.69-1.61 (m, 1H), 1.45-1.37 (m, 1H), 1.37 (s, 9H); ¹³C NMR (75 MHz, CDCl₃) δ=157.2, 80.1, 65.4, 58.9, 49.5, 35.0, 28.5; HRMS (ESI) calculated for [C₉H₁₉NO₄Na]⁺ (M+Na⁺) requires ink=228.1207, found 228.1201.

C.

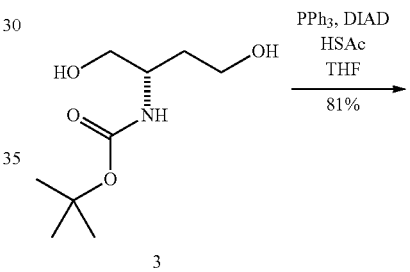

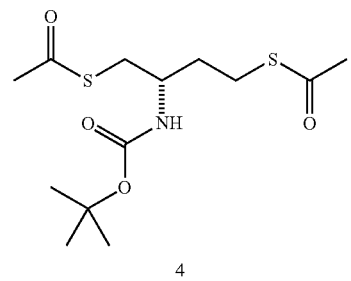

A dry round-bottom flask was charged with triphenylphosphine (1.711 g, 6.523 mmol) and placed under an atmosphere of dry N₂(g). Anhydrous THF (27 mL) was then added, and the solution was placed in an ice bath and cooled to 0° C. Diisopropyl azodicarboxylate (1.3 mL, 6.6 mmol) was added drop-wise to the flask. Once the addition was complete, the reaction mixture was allowed to stir for an additional 20 min. Compound 3 (0.559 g, 2.72 mmol) in 10 mL of dry THF and thioacetic acid (0.47 mL, 6.6 mmol) was then added with stirring. The reaction mixture was stirred at 0° C. for 1 h, and then at room temperature for 16 h. (Longer reaction times resulted in lower yields.) The mixture was concentrated under reduced pressure. Flash chromatography (30% v/v ethyl acetate in hexanes) was used to isolate 4 [(S)-S,S'-2-(tert-butoxycarbonylamino)butane-1,4-diyl diethanethioate] as a white solid (0.711 g, 81%). Compound 4 has been prepared form L-aspartic acid by a different route.[10a]

$^1$H NMR (400 MHz, CDCl$_3$) δ=4.59 (d, J=7.9 Hz, 1H), 3.85-3.76 (m, 1H), 3.12-2.95 (m, 3H), 2.82 (ddd, J=13.7, 8.5, 7.1 Hz, 1H), 2.36 (s, 3H), 2.33 (s, 3H), 1.84-1.75 (m, 1H), 1.74-1.64 (m, 1H), 1.44 (s, 9H); $^{13}$C NMR (75 MHz, CDCl$_3$) δ=195.9, 195.6, 155.6, 79.7, 50.1, 34.5, 33.8, 30.73, 30.71, 28.5, 25.9; HRMS (ESI) calculated for [C$_{13}$H$_{23}$NO$_4$S$_2$Na]$^+$ (M+Na$^+$) requires ink=344.0961, found 344.0962.

D.

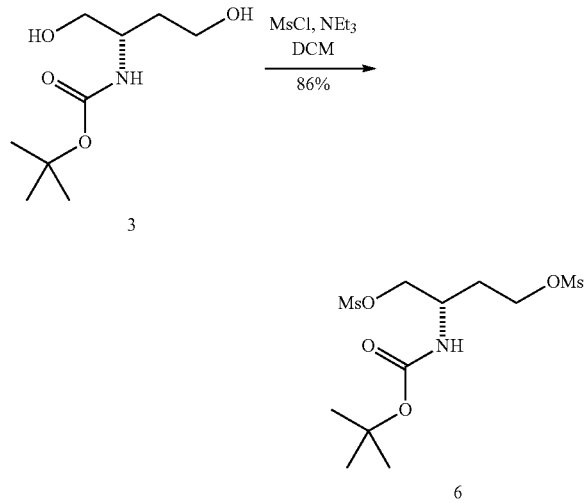

A dry round-bottom flask was charged with 3 (1.178 g, 5.739 mmol) and placed under dry N$_2$(g), Anhydrous DCM (125 mL) was then added, and the solution was cooled to 0° C. Triethylamine (4.0 mL, 29 mmol) was added, followed by slow drop-wise addition of methanesulfonyl chloride (MsCl) (1.0 mL, 13 mmol). After stirring at 0° C. for 30 min, the reaction mixture was allowed to warm slowly to room temperature and left to react for an additional 30 min. The reaction mixture was quenched by the addition 100 mL of water, and extracted with DCM. The combined organic extracts were washed with brine, dried over MgSO$_4$(s), and concentrated under reduced pressure. Flash chromatography (60% v/v ethyl acetate in hexanes) was used to isolate 6 [(S)-2-(tert-butoxycarbonyamino)butane-1,4-diyl dimethanesulfonate] as a white solid (1.782 g, 86%).

$^1$H NMR (400 MHz, CDCl$_3$) δ=4.81 (d, J=9.7 Hz, 1H), 4.39-4.26 (m, 4H), 4.10-4.05 (m, 1H), 3.06 (s, 3H), 3.05 (s, 3H), 2.13-1.96 (m, 2H), 1.48 (s, 9H); $^{13}$C NMR (75 MHz, CDCl$_3$) δ=155.4, 80.6, 71.0, 66.3, 47.0, 37.7, 37.6, 31.2, 28.5; HRMS (ESI) calculated for [C$_{11}$H$_{23}$NO$_8$S$_2$Na]$^+$ (M+Na$^+$) requires ink=384.0758, found 384.0775.

E.

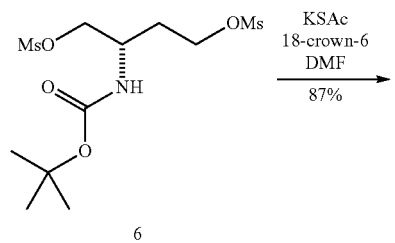

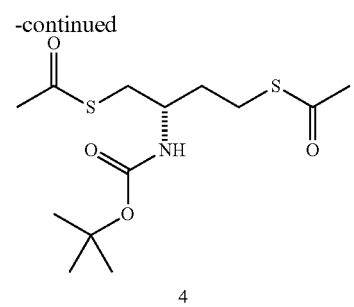

Compound 6 (0.610 g, 1.688 mmol), potassium thioacetate (0.482 g, 4.22 mmol), and 18-crown-6 (1.351 g, 5.111 mmol) were added to a dry round-bottom flask and dissolved with 150 mL of anhydrous DMF. The reaction mixture was stirred under dry N$_2$(g) for 24 h. The DMF was removed under reduced pressure. Flash chromatography (30% v/v ethyl acetate in hexanes) was used to isolate 4 [(S)—S,S'-2-(tert-butoxycarbonylamino)butane-1,4-diyl diethanethioate] as a white solid (0.475 g, 87%). Compound 4 has been prepared from L-aspartic acid by a different route. [10a]

$^1$H NMR (400 MHz, CDCl$_3$) δ=4.59 (d, J=7.9 Hz, 1H), 3.85-3.76 (m, 1H), 3.12-2.95 (m, 3H), 2.82 (ddd, J=13.7, 8.5, 7.1 Hz, 1H), 2.36 (s, 3H), 2.33 (s, 3H), 1.84-1.75 (m, 1H), 1.74-1.64 (m, 1H), 1.44 (s, 9H); $^{13}$C NMR (75 MHz, CDCl$_3$) δ=195.9, 195.6, 155.6, 79.7, 50.1, 34.5, 33.8, 30.73, 30.71, 28.5, 25.9; HRMS (ESI) calculated for [C$_{13}$H$_{23}$NO$_4$S$_2$Na]$^+$ (M+Na$^+$) requires ink=344.0961, found 344.0962.

F.

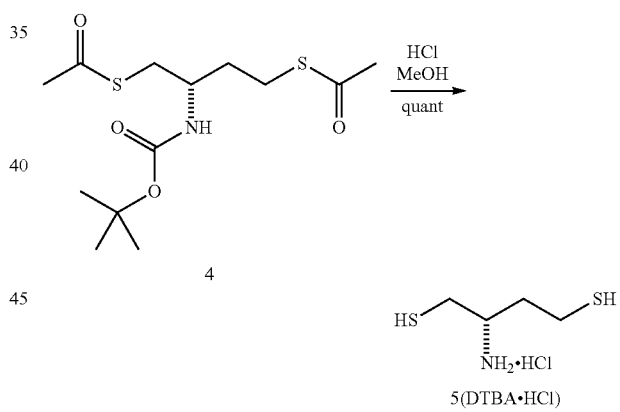

Compound 4 (0.601 g, 1.87 mmol) was added to a flame-dried round-bottom flask under dry N$_2$(g). Anhydrous methanol (20 mL) was added, followed by 10 mL of 3 N HCl in methanol. The reaction mixture was heated at reflux for 4 h, concentrated under reduced pressure, and stored in vacuo with P$_2$O$_5$ and KOH for 48 h. [2a] (Scratching the bottom of the flask facilitated crystal formation.) Compound 5, (2S)-2-amino-1,4-dimercaptobutane hydrochloride, herein S-dithiobutylamine hydrochloride (5-DTBA.HCl) was rinsed with cold toluene, and isolated by vacuum filtration as a white solid (0.320 g, quant). S-DTBA made in this manner was determined to be 99% pure according to Ellman's assay for sulfhydryl groups (vide infra). [24]

$^1$H NMR (400 MHz, DMSO-d$_6$) δ=8.29 (s, 3H), 3.34-3.32 (m, 1H), 2.96 (t, J=8.7 Hz, 1H), 2.81-2.75 (m, 2H), 2.60-2.56 (m, 3H), 1.95-1.86 (m, 2H); $^{13}$C NMR (75 MHz, DMSO-d$_6$)

δ=51.2, 35.0, 26.0, 19.6; HRMS (ESI) calculated for [$C_4H_{12}NS_2$]$^+$ (M$^+$) requires m/z=138.0406, found 138.0405.

G.

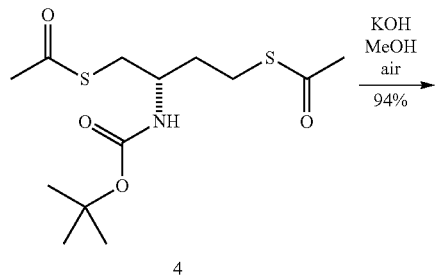

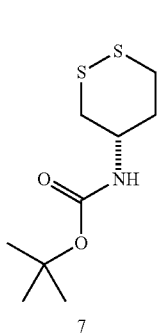

Compound 4 (0.482 g, 1.50 mmol) and potassium hydroxide (0.340 g, 6.06 mmol) were dissolved in 50 mL of methanol, and the resulting solution was stirred for 16 h while bubbling a light stream of air through the solution. The methanol was removed under reduced pressure, and the mixture was extracted with DCM, washed with brine, and dried over MgSO$_4$(s). Flash chromatography (20% v/v ethyl acetate in hexanes) was used to isolate 7 [(S)-tert-butyl 1,2-dithian-4-ylcarbamate] as a white solid (0.331 g, 94%).

$^1$H NMR (400 MHz, DMSO-d$_6$) δ=7.08 (d, J=7.9 Hz, 1H), 3.53-3.41 (m, 1H), 3.07-3.01 (m, 1H), 2.91-2.85 (m, 2H), 2.60 (dd, J=13.0, 10.5 Hz, 1H), 2.08-2.03 (m, 1H), 1.67-1.57 (m, 1H), 1.38 (s, 9H); $^{13}$C NMR (75 MHz, DMSO-d$_6$) δ=155.2, 78.7, 49.3, 37.9, 34.9, 34.5, 28.9; HRMS (ESI) calculated for [$C_9H_{17}NO_2S_2$]$^+$ (M$^+$) requires m/z=258.0593, found 258.0602.

F.

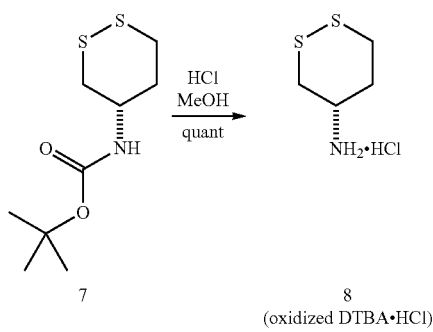

Compound 7 (0.402 g, 1.71 mmol) was added to a round-bottom flask. Anhydrous methanol (20 mL) was added, followed by 10 mL of 3 N HCl in methanol. The reaction mixture was heated at reflux for 4 h under N$_2$(g), concentrated under reduced pressure, and stored in vacuo with P$_2$O$_5$ and KOH for 24 h. (Scratching the bottom of the flask facilitated crystal formation.) Compound 8, oxidized DTBA·HCl [(S)-1,2-dithian-4-amine hydrochloride], was isolated as a white solid (0.289 g, quant).

$^1$H NMR (400 MHz, DMSO-d$_6$) δ=8.29 (s, 3H), 3.43-3.37 (m, 1H), 3.15-3.08 (m, 2H), 3.02-2.96 (m, 1H), 2.88 (dd, J=13.1, 10.6 Hz, 1H), 2.32-2.28 (m, 1H), 1.85-1.77 (m, 1H); $^{13}$C NMR (75 MHz, DMSO-d$_6$) δ=48.7, 34.6, 32.8, 31.5; HRMS (ESI) calculated for [$C_4H_{10}NS_2$]$^+$ (M$^+$) requires m/z=136.0250, found 136.0249.

Example 3

Purity of DTBA Assessed by Ellman's Assay for Sulfhydryl Groups

A reaction buffer (0.10 M sodium phosphate buffer, pH 8.0, containing 1 mM EDTA) was prepared by the Pierce protocol. Ellman's reagent solution was primed by adding Ellman's reagent (4 mg) to 1 mL of the reaction buffer. A 2.50×10$^{-4}$ M solution of DTBA was then prepared using the reaction buffer. Ellman's reagent solution (50 µL) was added to each of two vials containing 2.5 mL of reaction buffer. Reaction buffer (250 µL) was added to one of these vials, and its absorbance at 412 nm was used as a blank. DTBA solution (250 µL) was added to the other vial. After 10 min, its absorbance at 412 nm was recorded. Using Beer's law (c=A/(ε·l) with A=0.623, l=1 cm, and ε=14,150 M$^{-1}$cm$^{-1}$) gave a thiol concentration of 4.40×10$^{-5}$ M. Because DTBA contains two thiol groups, the assay solution had a DTBA concentration of 2.20×10$^{-5}$ M. Accounting for dilution and using the equation $M_1 \cdot V_1 = M_2 \cdot V_2$, where $V_1$=2.50×10$^{-4}$ L, $M_2$=2.20×10$^{-5}$ M, and $V_2$=2.8×10$^{-3}$ L, yielded $M_1$=2.46×10$^{-4}$ M and thus a DTBA purity of (2.46×10$^{-4}$ M)/(2.50×10$^{-4}$ M)×100%=98.4%. Three repetitions of this assay gave (99±1)% purity. This assay revealed that commercial DTT and BMS had >98% purity.

Example 4

Determination of Thiol pK$_a$ Values

Figure 3:
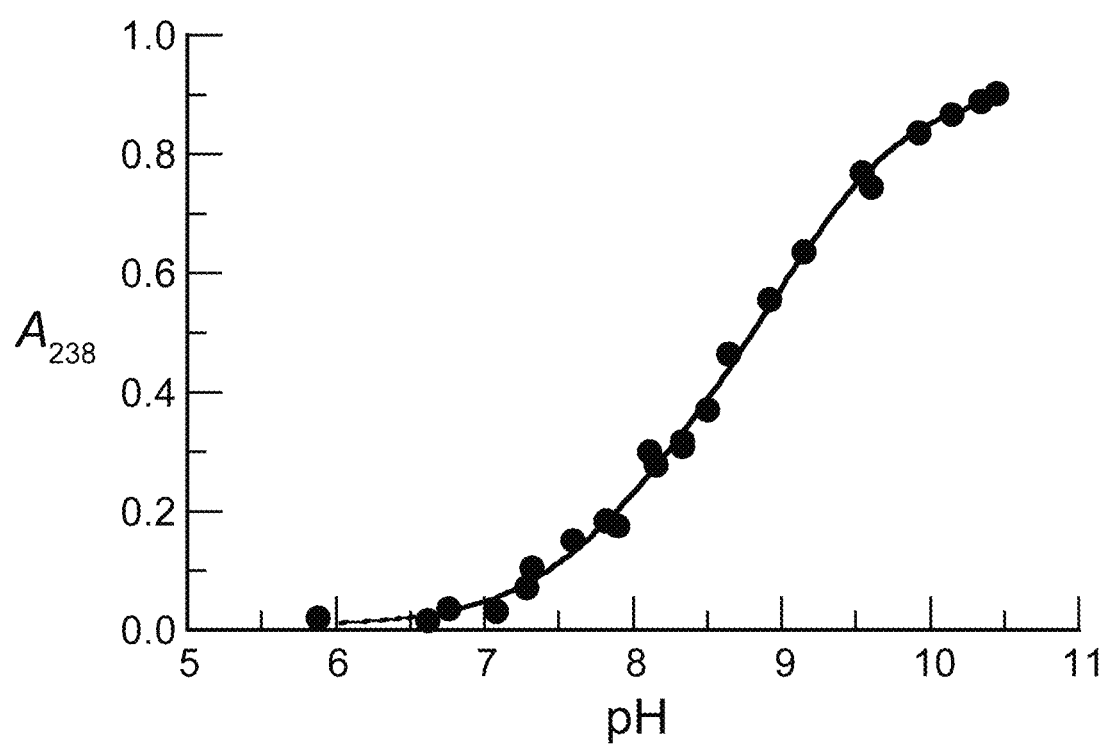
FIG. 3 is a graph showing the effect of pH on absorbance at 238 nm ($A_{238}$) of DTBA (0.10 mM) in 0.10 M potassium phosphate buffer. Fitting the data to eq 1 yielded $pK_a$ values of 8.2±0.2 and 9.3±0.1, and extinction coefficients of $\epsilon_{SH}^{SH}=83.27 M^{-1} cm^{-1}$, $\epsilon_{SH}^{S^-}=3436 M^{-1} cm^{-1}$, and $\epsilon_{S^-}^{S^-}=M^{-1} cm^{-1}$ with $r^2>0.99$.
Figure 4:
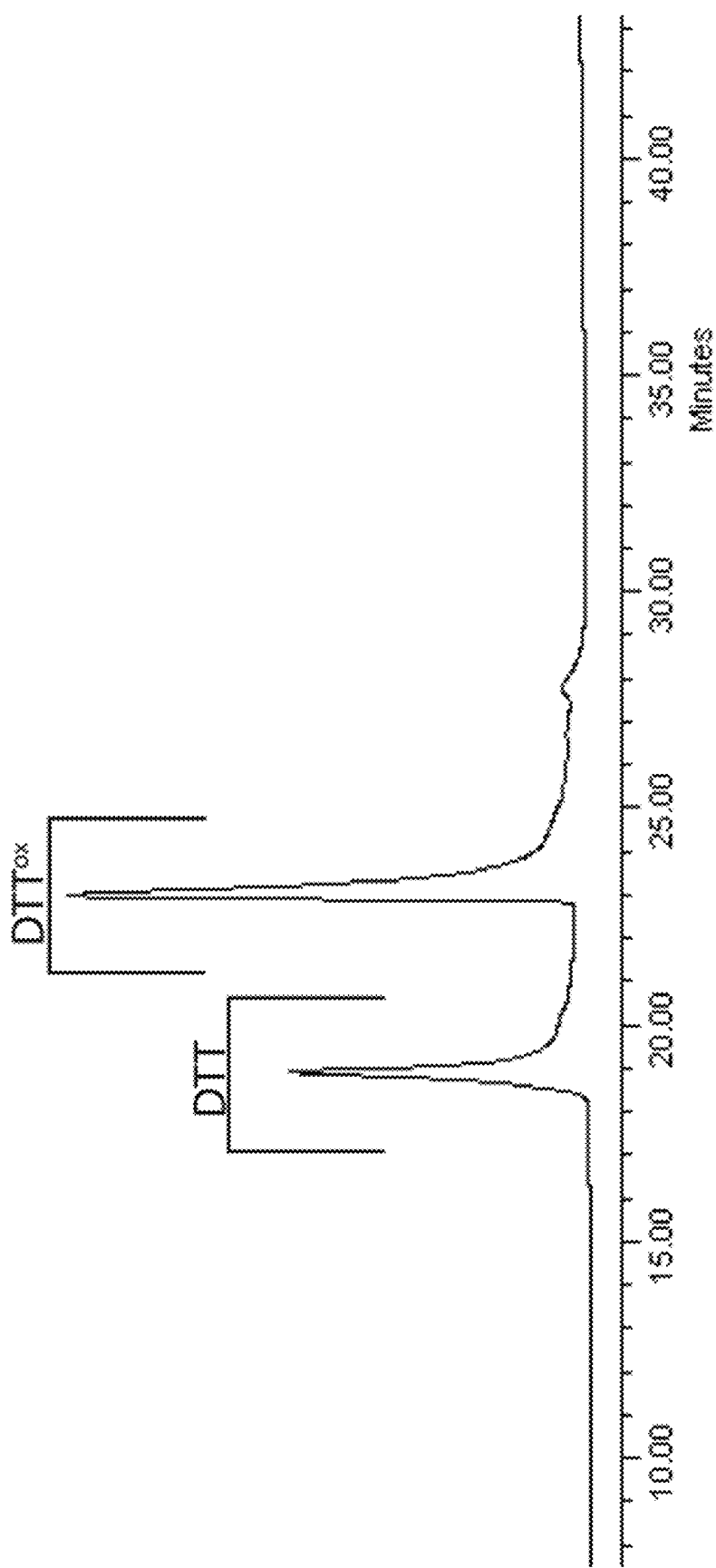
FIG. 4 illustrates a representative HPLC chromatogram of the redox equilibrium between DTBA and DTT. Compounds were detected by their absorbance at 205 nm.

The thiol pK$_a$ values of DTBA were determined by measuring its absorbance at 238 nm in solutions of different pH. The deprotonated thiolate absorbs much more strongly at 238 nm than does its protonated counterpart. [15a] This attribute was exploited for determining thiol pK$_a$ values as described previously. [15b] Buffered stock solutions of K$_3$PO$_4$, K$_2$HPO$_4$, and KH$_2$PO$_4$ (100 mM) were degassed and flushed with N$_2$(g) for 1 h immediately prior to use. A stock solution of DTBA (1.5 mM) in KH$_2$PO$_4$ was then prepared. Various combinations of the buffered stock solutions were combined in duplicate to give two identical sets of 1-mL solutions of pH 5.5-11. KH$_2$PO$_4$ stock solution (70 µL) was added to each replicate pair of solutions and used to set the A$_{238}$ to zero. Dithiol solution (70 µL) was then added to its complimentary 1-mL vial, and its absorbance at 238 nm was recorded. The pH of the solution was then immediately measured using a Beckman pH meter, which had been calibrated prior to use with pH 7 and pH 10 standard solutions from Fisher Scientific. This process was repeated multiple times to obtain a plot of A$_{238}$ vs pH (FIG. 3).

pK$_a$ values were determined by fitting the data in FIG. 3 to eq 1, which is derived from Beer's law and the definition of the acid dissociation constant. [15b] In eq 1, C$_T$ is total thiol concentration, $\epsilon_{SH}^{SH}$ is the extinction coefficient of the doubly protonated form, $\epsilon_{SH}^{S-}$ is the extinction coefficient of the singly protonated form, and $\epsilon_{S-}^{S-}$ is the extinction coefficient of the unprotonated form. Both $pK_a$ values and extinction coefficients were determined from the curve fit.

$$A_{238} = C_T \left( \frac{\varepsilon_{S^-}^{S^-} 10^{pH-pK_{a2}} + \varepsilon_{SH}^{S^-} + \varepsilon_{SH}^{SH} 10^{pK_{a1}-pH}}{10^{pH-pK_{a2}} + 1 + 10^{pK_{a1}-pH}} \right) \quad (1)$$

Example 5

Reduction Potential of DTBA

The reduction potential ($E^{o\prime}$) of DTBA was determined by using HPLC to determine the equilibrium constant for its reaction with oxidized DTT (eq 2), and then inserting this value into a variation of the Nernst equation (eq 3). [2g] Data were obtained by a procedure similar to that described previously. [2g, 15b] DTBA (10.5 mg, 0.06 mmol) and oxidized DTT (9.2 mg, 0.06 mmol) were added to a 25-mL round-bottom flask. The flask was then flushed with $N_2(g)$ for 30 min.

$$K_{eq} = \frac{[DTT][\text{oxidized } DTBA]}{[DTBA][\text{oxidized } DTT]} = \frac{[DTT]^2}{[\text{oxidized } DTT]^2} \quad (2)$$

$$E^{o\prime}_{DTBA} = E^{o\prime}_{DTT} - \frac{RT}{nF} \ln \frac{[DTT]^2}{[\text{oxidized } DTT]^2} \quad (3)$$

A 50 mM stock solution of potassium phosphate buffer (pH 7) was degassed and purged with $N_2(g)$ for 30 min immediately prior to use. Buffer (15 mL) was added, and the reaction mixture was stirred under $N_2(g)$ for 24 h at room temperature. The reaction mixture was then quenched by the addition of 3 N HCl (1:100 dilution). The reaction mixture was passed through a 4.5-μm filter, and 100 μL of the reaction mixture was analyzed immediately by HPLC using a Waters system equipped with a Waters 996 photodiode array detector, Empower 2 software, and a Varian C18 reverse-phase column. The column was eluted at 1.0 mL/min with water (5.0 mL), followed by a linear gradient (0-40% v/v) of acetonitrile/water over 40 min. Compounds were detected by their absorbance at 205 nm. Reduced and oxidized DTBA are highly polar and elute from the column immediately (as confirmed by LC-MS). Two peaks, however, were clearly visible in the chromatogram FIG. 4). HPLC analysis of standards revealed that the two peaks were reduced DTT (retention time: 19 min) and oxidized DTT (retention time: 23 min). Calibration curves were generated and found to be linear over the used concentration range. From these curves, the equilibrium concentrations of reduced and oxidized DTT were determined, and a $K_{eq}$=0.469±0.131 for the reaction was found. Assuming that DTT has $E^{o\prime}$=−0.327 V, [2a] eq 3 (which is a variation of the Nernst equation) was used to calculate that DTBA has $E^{o\prime}$=−(0.317±0.002) V. This value is the mean±SE from seven experiments. The reverse reaction between oxidized DTBA and reduced DTT revealed that equilibrium had been established under the experimental conditions.

Example 6

Reduction Potential of BMS

The procedure described in Example 5 was also performed with BMS. With $K_{eq}$=0.0517±0.0194 and assuming $E^{o\prime}$=−0.327 V for DTT, [2a] BMS was found to have $E^{o\prime}$=(−0.291±0.002) V, which was again the mean±SE from seven experiments. A previously reported reduction potential for BMS was $E^{o\prime}$=−0.31 V. [2g]

Example 7

Kinetic Studies on the Reduction of Oxidized βME $$-\frac{\partial [\text{disulfide}]_{total}}{\partial t} = k_{obs} [\text{disulfide}]_{total} [\text{thiol}]_{total}$$

The observed second-order rate constant ($k_{obs}$) for a thiol-disulfide interchange reaction was determined by adapting a procedure described previously. [2e] When the disulfide is oxidized βME, a 50 mM stock solution of potassium phosphate buffer was degassed and purged with $N_2(g)$ for 30 min immediately prior to use. A stock solution of oxidized βME (10 mM) in 50 mM potassium phosphate buffer, pH 7.0, was purged with $N_2(g)$ for 30 min immediately prior to use. A 25-mL round-bottom flask was charged with DTBA (4.3 mg, 0.025 mmol) or DTT (3.9 mg, 0.025 mmol), and placed under $N_2(g)$. Phosphate buffer (2.5 mL) was added to the round-bottom flask containing the dithiol. Oxidized βME stock solution (2.5 mL) was then added, and the reaction mixture was stirred at room temperature under $N_2(g)$ for 1 min. The reaction mixture was quenched by the addition of 0.10 mL of 3 N HCl. The reaction mixture was passed through a 4.5-μm filter, and 100 μL of the reaction mixture was analyzed immediately by HPLC using a Varian C18 reverse-phase column. The column was eluted at 1.0 mL/min with water (5.0 mL), followed by a linear gradient (0-40% v/v) of acetonitrile/water over 40 min. The extent of reduction was determined by integrating the newly formed peak corresponding to βME at 205 nm (retention time: 8 min). This process was repeated for reaction times of 2 and 4 min. Calibration curves were generated and found to be linear over the used concentration range. The amount of residual oxidized βME was calculated, and second-order rate constants were calculated from a linear fit of the data in FIG. 1A (that is, $k_{obs}$=[(1/$c_{final}$)−(1/$c_{initial}$)]/t). The initial values of concentration in the reaction mixture were [DTBA or DTT]=[oxidized βME]=$c_{intitial}$=5 mM. Rate constants were the mean±SE from three experiments. DTBA: $k_{obs}$=(0.29±0.02) $M^{-1}s^{-1}$ and DTT: $k_{obs}$=(0.084±0.004) $M^{-1}s^{-1}$. The same procedure was performed for reactions at pH 5.5, giving DTBA: $k_{obs}$=(0.0093±0.0003) $M^{-1}s^{-1}$ and DTT: $k_{obs}$=(0.0021±0.0002) $M^{-1}s^{-1}$ (FIG. 1A).

Example 8

Kinetic Studies on the Reduction of Oxidized L-Glutathione

An experiment similar to that in Example 7 was conducted with disulfide=oxidized L-glutathione. Reactions were quenched at various time points (2, 4, 6, and 8 min) and 100 μL was analyzed by HPLC (1.0 mL/min with water (5.0 mL) in 0.1% v/v TFA, followed by a linear gradient (0-40% v/v) of acetonitrile in 0.1% v/v TFA over 40 min). The extent of reduction was determined by integrating the newly formed L-glutathione reduced peak at 220 nm (retention time of 7 min). Second-order rate constants were calculated from a linear fit of the data in FIG. 1B (that is, $k_{obs}$=[(1/$c_{final}$)−

$(1/c_{initial})]/t)$. Rate constants were the mean±SE from three experiments. DTBA: $k_{obs}$=(0.83±0.04) $M^{-1}s^{-1}$ and DTT: $k_{obs}$=(0.16±0.02) $M^{-1}s^{-1}$.

Example 9

Kinetic Studies on the Reactivation of Papain

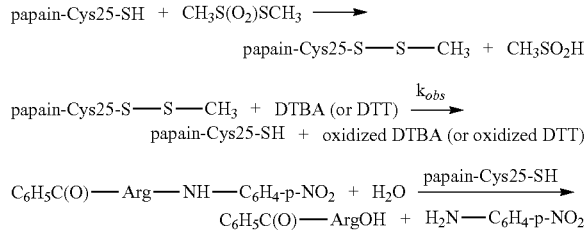

Cys25 in the active site of papaya latex papain was oxidized as a mixed disulfide by a procedure described previously.[25] Briefly, a stock solution of methyl methanethiosulfonate (3.5 mM) was prepared by dilution of 5 μL of methyl methanethiosulfonate with 15 mL of 0.10 M potassium phosphate buffer, pH 7.0, containing EDTA (2 mM). KCl (0.011 g, 0.15 mmol) was added to 1.5 mL of this stock solution. The solution was deoxygenated by bubbling $N_2(g)$ through it for 15 min. Next, papain (5 mg, 150 units) was added, and the resulting solution was incubated at room temperature under $N_2(g)$ for 12 h. Excess methyl methanethiosulfonate was removed by size-exclusion chromatography using a Sephadex G-25 column. The final concentration of papain was determined by $A_{280}$ using $\epsilon_{280}$=5.60×10⁴ $M^{-1}cm^{-1}$. [26] A solution (0.26 mL) of the chromatographed protein was diluted with 4.94 mL of deoxygenated aqueous buffer (0.10 M imidazole-HCl buffer, pH 7.0, containing 2 mM EDTA). Enzyme solution (1.25 mL) was then added to four separate vials. DTBA or DTT (10 μL of a 1 mM solution) was added to one of the vials, and a timer was started. The initial concentrations in the reaction mixture were dithiol reducing agent: 7.9×10⁻⁶ M and inactive protein: 4.9×10⁻⁶ M. At various times, an 0.20-mL aliquot was removed from the reaction mixture and added to a cuvette of 0.8 mL of substrate solution (1.25 mM N-benzoyl-L-arginyl-p-nitroanilide in 0.10 M imidazole-HCl buffer, pH 6.0, containing 2 mM EDTA). The rate of change in absorbance at 410 nm was recorded at 25° C. A unit of protein is defined by the amount of enzyme required to produce 1 μmol/min of 4-nitroaniline. Using an extinction coefficient for 4-nitroaniline of $\epsilon$=8,800 $M^{-1}cm^{-1}$ at 410 nm, [27] the number of units of active papain in solution at each time point was calculated. To determine the possible number of units of active papain in the reaction mixture, a large excess of DTT (~10³-fold) was added to one vial and the activity was assessed. As a control, it was determined that the concentrations of DTT used had no bearing on the assay data other than activating the protein. Enzymatic activity (%) at particular times was calculated by dividing the number of active units of enzyme by the possible number of units in the solution, and was plotted as in FIG. 2A. To determine the value of the second-order rate constant $k_{obs}$ for the reducing agents, the second-order rate equation (eq 4) was transformed into eq 5, which was fitted to the data with the program PRISM 5.0. In eq 4 and 5, $A_0$=[inactive protein]$_{t=0}$, A=[inactive protein]$_t$= $A_0$-$A_0$y, $B_0$=[reducing agent]$_{t=0}$, and B=[reducing agent]$_t$=

$B_0$-$A_0$y. Values of $k_{obs}$ were the mean±SE from three experiments. DTBA: $k_{obs}$=(1342±148) $M^{-1}s^{-1}$ and DTT: $k_{obs}$=(91.3±9.4) $M^{-1}s^{-1}$.

$$\frac{1}{B_0 - A_0} \ln \frac{A_0 B}{A B_0} = k_{obs} t \quad (4)$$

$$y = \frac{B_o - B_o e^{k_{obs} t (A_o - B_o)}}{B_o - A_o e^{k_{obs} t (A_o - B_o)}} \times 100\% \quad (5)$$

Example 10

Kinetic Studies on the Reactivation of Creatine Kinase

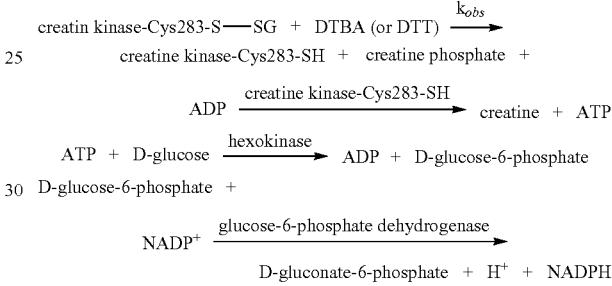

Cys283 in the active site of rabbit muscle creatine kinase was oxidized as a mixed disulfide by a procedure described previously, [28] but with a slight modification in the measurement of active enzyme. A unit of enzyme was defined as the amount required to produce 1 μmol/min of NADPH. Using an extinction coefficient for NADPH of $\epsilon$=6.22 $mM^{-1}cm^{-1}$ at 340 nm, the units of active creatine kinase in solution at a particular time were calculated. To determine the possible number of units of active creatine kinase in the reaction mixture, a large excess of DTT (~10³-fold) was added to one vial and the activity was assessed. As a control, it was determined that the concentrations of DTT used had no bearing on the assay data other than activating the protein. Enzymatic activity (%) at particular times was calculated by dividing the number of active units of enzyme by the possible number of units in the solution, and was plotted as in FIG. 2B. Values of the second-order rate constant k were determined by using eq 4 as described in Example 9, and were the mean±SE from three experiments. DTBA: $k_{obs}$=(15.1±1.0) $M^-s^{-1}$ and DTT: $k_{obs}$=(17.5±1.6) $M^{-1}s^{-1}$.

Example 11

Separation of DTBA Using an Ion-Exchange Resin

A reaction buffer (0.10 M sodium phosphate, pH 8.0, 1 mM EDTA) was prepared. Ellman's reagent solution was prepared by adding Ellman's reagent (4 mg) to 1 mL of the reaction buffer. Next, to 25 mL of reaction buffer (0.10 M sodium phosphate, pH 8.0, 1 mM EDTA) was added DTBA (2.2 mg, 1.27×10⁻⁵ mol) and 1.7 g of DOWEX 50WX4-400 ion-exchange resin. The mixture was swirled for several minutes and filtered through a fritted syringe. Ellman's reagent solution (50 µL) was added to two separate vials containing 2.5 mL of reaction buffer. As a blank, 250 µL of reaction buffer was added to one of the vials, and the absorbance at 412 nm was set to zero. Filtrate (250 µL) was then added to the other vial and its absorbance was recorded. With $A_{412}=0.012$ and using an extinction coefficient of $\epsilon=14,150$ $M^{-1}cm^{-1}$, [24b, 24c] it was calculated that >99% of DTBA was retained by the resin and thus removed from solution. The same assay was repeated with DTT, resulting in <1% being removed from solution. See Example 3 for a more detailed explanation of similar calculations using Ellman's assay.

Example 12

Ultraviolet Spectra of Oxidized DTBA and Oxidized DTT

Figure 6:
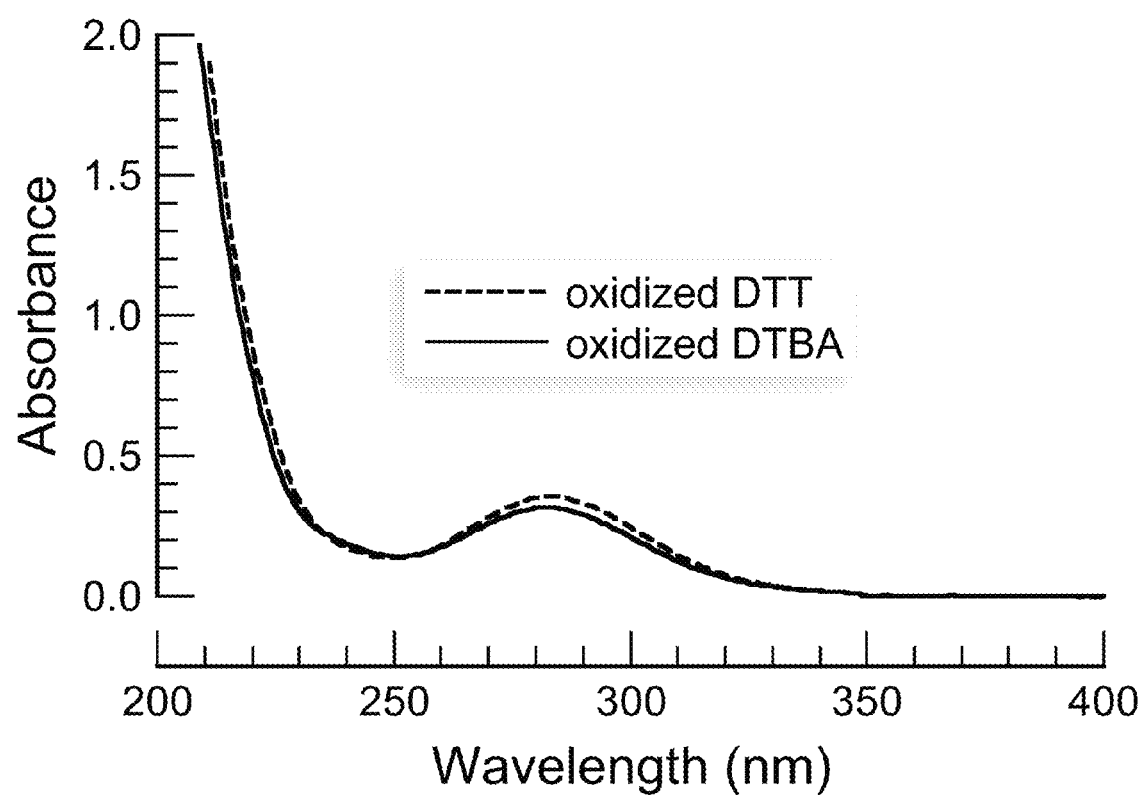
FIG. 6 illustrates the ultraviolet spectrum of oxidized DTBA and oxidized DTT in DPBS.

Solutions of oxidized DTBA and DTT (1.0 mM) were prepared in Dulbecco's phosphate buffered saline (DPBS), and their ultraviolet spectra were recorded (FIG. 6).

Example 13

Preparation of Immobilized Dithiobutylamine (DTBA)

A. Coupling of DTBA$^{ox}$ to Preactivated TentaGel® Resin

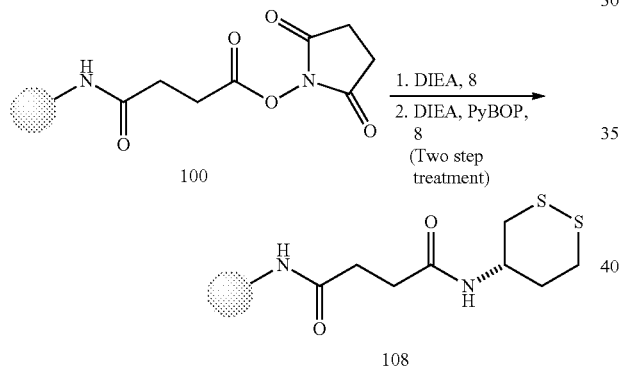

Preactivated succinimidyl ester resin (1 g, ~0.21 mmol/g) with a particle size of 130 µm and capacity of 0.2-0.3 mmol/g (TentaGel®COOSu, Rapp Polymere GmbH, Tuebingen, Germany) was placed in a solid phase peptide synthesis vessel. As a pretreatment, the resin was allowed to swell in 5 mL of N-methyl-2-pyrrolidone (NMP) for five min. while bubbling nitrogen through the solution. The NMP was then removed by vacuum filtration and the process was repeated two more times. The resin used in this example is a grafted copolymer with a cross-linker polystyrene matrix on which polyethylene glycol (PEG or POE) is grafted and the PEG spacer is in the range of MW 3000 Da. To the resin was then of added 10 mL of NMP, 0.320 mL (1.8 mmol) of N,N-diisopropylethylamine (DIEA), and 0.1224 g (0.7128 mmol) of compound 8 (DTBA$^{ox}$). The resulting mixture was allowed to react for 60 min while bubbling nitrogen through the solution. The solution was then removed by vacuum filtration and the resin was washed three times with 5 mL of NMP. In a second coupling step, 10 mL of NMP, 0.470 g (0.903 mmol) of Benzotriazol-1-yl-oxytripyrrolidinophosphonium hexafluorophosphate (PyBOP), 0.320 mL (1.8 mmol) of DIEA and 0.1224 mg (0.7128 mmol) of compound 8 were added to the resin and allowed to react for an additional hour while bubbling nitrogen through the solution. The solution was then removed by vacuum filtration.

B. Reduction/Regeneration of Immobilized DTBA$^{ox}$ (3 Methods)

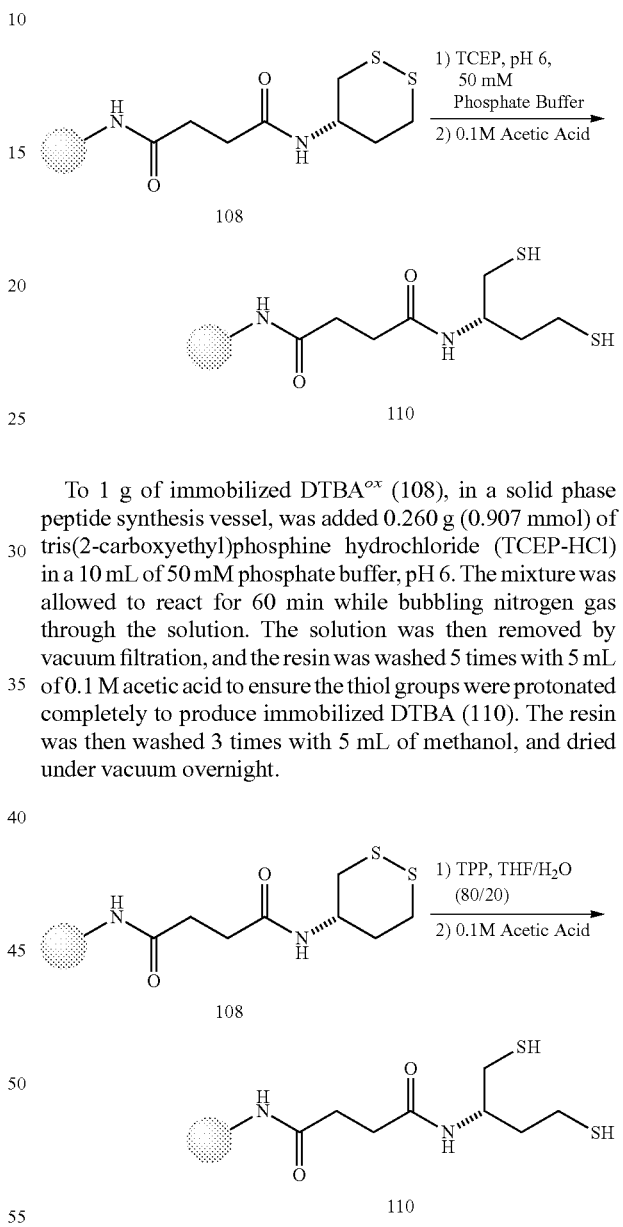

To 1 g of immobilized DTBA$^{ox}$ (108), in a solid phase peptide synthesis vessel, was added 0.260 g (0.907 mmol) of tris(2-carboxyethyl)phosphine hydrochloride (TCEP-HCl) in a 10 mL of 50 mM phosphate buffer, pH 6. The mixture was allowed to react for 60 min while bubbling nitrogen gas through the solution. The solution was then removed by vacuum filtration, and the resin was washed 5 times with 5 mL of 0.1 M acetic acid to ensure the thiol groups were protonated completely to produce immobilized DTBA (110). The resin was then washed 3 times with 5 mL of methanol, and dried under vacuum overnight.

To 1 g of immobilized DTBA$^{ox}$ (108), in a solid-phase peptide synthesis vessel, was added 0.551 g (2.1 mmol) of triphenylphosphine (TPP) in 10 mL of H$_2$O/THF (80:20). The mixture was allowed to react for 60 min while bubbling nitrogen gas through the solution. The solution was then removed by vacuum filtration, and the resin was washed 5 times with 5 mL of 0.1 M acetic acid to ensure the thiol groups were completely protonated to generate immobilized DTBA (110). The resin was then washed 3 times with 5 mL of methanol, and dried under vacuum overnight.

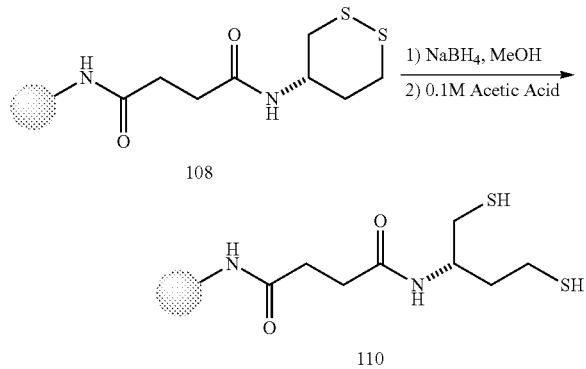

To 1 g immobilized DTBA$^{ox}$ (108), in a solid phase peptide synthesis vessel, was added 79.4 mg (2.10 mmol) of NaBH$_4$ in 10 mL of methanol. Nitrogen has was bubbled through the solution, while the mixture was allowed to react. After 60 min, the solution was removed by vacuum filtration and washed 5 times with 5 mL of 0.1 M acetic acid to ensure the thiol groups were completely protonated to generate immobilized DBTA (110). The resin was then washed 3 times with 5 mL of methanol, and dried under vacuum overnight.

The above procedures were performed multiple times with yields of immobilized DTBA ranging from 75-93%, as determined by Ellman's assay for sulfhydryl groups.

Figure 5:
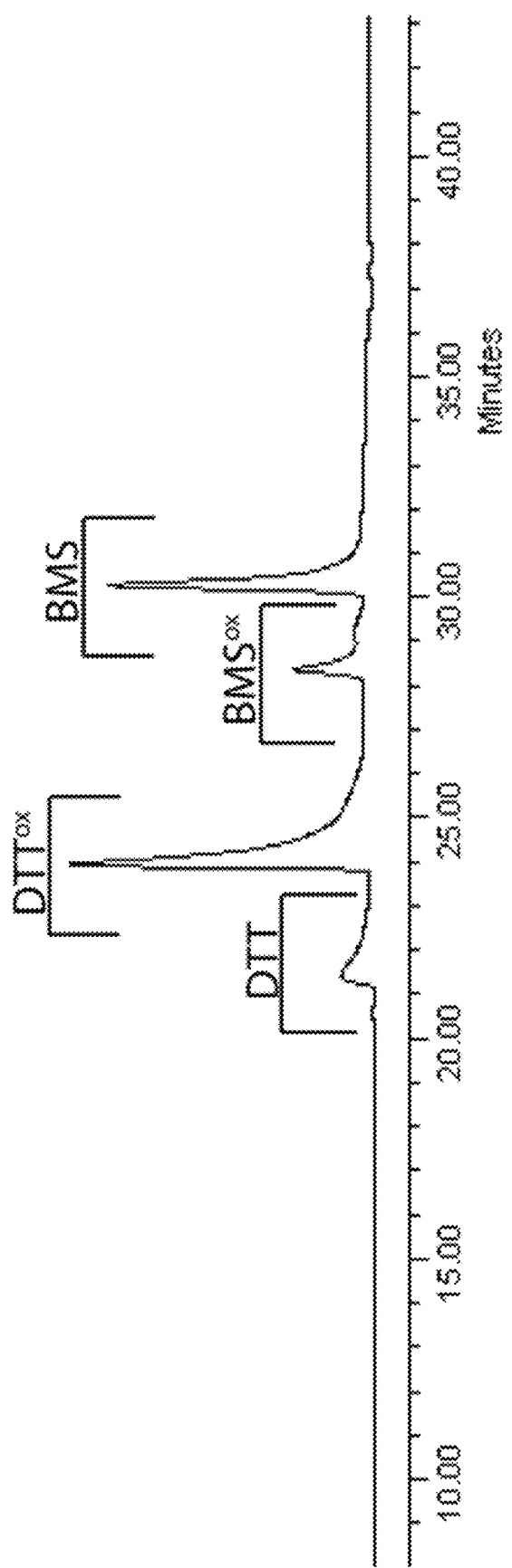
FIG. 5 illustrates a representative HPLC chromatogram of the redox equilibrium between BMS and DTT. Compounds were detected by their absorbance at 205 nm.

REFERENCES (1) Martelli, P. L.; Fariselli, P.; Cadadio, R. Proteomics 2004, 4, 1655-1671.
(2) (a) Cleland, W. W. Biochemistry 1964, 3, 480-482. (b) Jocelyn, P. C. Biochemistry of the SH Group: The Occurrence, Chemical Properties, Metabolism and Biological Function of Thiols and Disulphides; Academic Press: London, UK, 1972. (c) Smith, D. J.; Maggio, E. T.; Kenyon, G. L. Biochemistry 1975, 14, 766-771. (d) Ranganathan, S.; Jayaraman, N. Chem. Commun. 1991, 934-936. (e) Burns, J. A.; Butler, J. C.; Moran, J.; Whitesides, G. M. J. Org. Chem. 1991, 56, 2648-2650. (f) Lees, W. J.; Singh, R.; Whitesides, G. M. J. Org. Chem. 1991, 56, 7328-7331. (g) Lamoureux, G. V.; Whitesides, G. M. J. Org. Chem. 1993, 58, 633-641. (h) Singh, R.; Whitesides, G. M. Bioorg. Chem. 1994, 22, 109-115. (i) Gilbert, H. F. Methods Enzymol. 1995, 251, 8-28. (j) Singh, R.; Lamoureux, G. V.; Lees, W. J.; Whitesides, G. M. Methods Enzymol. 1995, 251, 167-173. (k) Getz, E. B.; Xiao, M.; Chakrabarty, T.; Cooke, R.; Selvin, P. R. Anal. Biochem. 1999, 273, 73-80. (l) Cline, D. J.; Redding, S. E.; Brohawn, S. G.; Psathas, J. N.; Schneider, J. P.; Thorpe, C. Biochemistry 2004, 43, 15195-15203.
(3) (a) Whitesides, G. M.; Lilburn, J. E.; Szajewski, R. P. J. Org. Chem. 1977, 42, 332-338. (b) Snyder, J. P.; Carlsen, L. J. Am. Chem. Soc. 1977, 99, 2931-2942. (c) Rosenfield, R. E.; Parthasarathy, R.; Dunitz, J. D. J. Am. Chem. Soc. 1977, 99, 4860-4862. (d) Shaked, Z.; Szajewski, R. P.; Whitesides, G. M. Biochemistry 1980, 19, 4156-4166. (e) Houk, J.; Whitesides, G. M. J. Am. Chem. Soc. 1987, 109, 6825-6836. (f) Keire, D. A.; Strauss, E.; Guo, W.; Noszal, B.; Rabenstein, D. L. J. Org. Chem. 1992, 57, 123-127. (g) Rothwarf, D. M.; Scheraga, H. A. Proc. Natl. Acad. Sci. USA 1992, 89, 7944-7948. (h) Fernandes, P. A.; Ramos, M. J. Chem.-Eur. J. 2004, 10, 257-266.
(4) βME is also an unstable, foul-smelling liquid 2f,3a,3d with a high reduction potential and high thiol pKa (Table 1).
(5) Evans, R. M.; Fraser, J. B.; Owen, L. N. J. Chem. Soc. 1947, 248-255.
(6) The current price of DTT is 102-fold greater per thiol group than that of βME (Sigma-Aldrich, St. Louis, Mo.).
(7) Tris(2-carboxyethyl)phosphine (TCEP) is more potent than DTT at reducing disulfide bonds between small molecules (see 2e), but not within proteins (see 21).
(8) Another commercial dithiol, bis(2-mercaptoethyl) sulfone (BMS), has low thiol pKa values of 7.9±0.2 and 9.0±0.2.2 g. Upon oxidation, however, BMS forms a seven-membered ring with E°'=(−0.291±0.002) V (FIG. 5), making BMS a less potent reducing agent than DTT.
(9) (a) Coppola, G. M.; Schuster, H. F. Asymmetric Synthesis: Construction of Chiral Molecules Using Amino Acids; John Wiley & Sons: New York, N.Y., 1987. (b) McCaldon, P.; Argos, P. Proteins 1988, 4, 99-122.
(10) Carbamate derivatives of DTBA are known. (a) Kessler, P.; Servent, D.; Hirth, C. Tetrahedron Lett. 1994, 35, 7237-7340. (b) Servent, D.; Menez, A.; Kessler, P. FEBS Lett. 1995, 360, 261-265.
(11) Mitsunobu, O.; Masahiko, E. Bull. Chem. Soc. Jpn. 1971, 44, 3427-3430.
(12) Jencks, W. P.; Salvesen, K. J. Am. Chem. Soc. 1971, 93, 4433-4436.
(13) Connett, P. H.; Wetterhahn, K. E. J. Am. Chem. Soc. 1986, 108, 1842-1847.
(14) Lees, W. J.; Whitesides, G. M. J. Org. Chem. 1993, 58, 642-647.
(15) (a) Benesch, R. E.; Benesch, R. J. Am. Chem. Soc. 1955, 77, 5877-5881. (b) Woycechowsky, K. J.; Wittrup, K. D.; Raines, R. T. Chem. Biol. 1999, 6, 871-879.
(16) The amino group of DTBA is assumed to be cationic throughout its pH-titration, as cysteamine has an amino pKa of 10.44 [see 13].
(17) Chivers, P. T.; Prehoda, K. E.; Raines, R. T. Biochemistry 1997, 36, 4061-4066.
(18) (a) Roberts, D. D.; Lewis, S. D.; Ballou, D. P.; Olson, S. T.; Shafer, J. A. Biochemistry 1986, 25, 5595-5601. (b) Singh, R.; Blattler, W. A.; Collinson, A. R. Anal. Biochem. 1993, 213, 49-56.
(19) (a) Schechter, I.; Berger, A. Biochem. Biophys. Res. Commun. 1967, 27, 157-162. (b) Pickersgill, R. W.; Harris, G. W.; Garman, E. Acta Crystallogr., Sect. B 1992, 48, 59-67.
(20) Rao, J. K. M.; Bujacz, G.; Wlodawer, A. FEBS Lett. 1998, 439, 133-137.
(21) (a) Putney, S.; Herlihy, W.; Royal, N.; Pang, H.; Aposhian, H. V.; Pickering, L.; Belagaje, R.; Biemann, K.; Page, D.; Kuby, S.; Schimmel, P. J. Biol. Chem. 1984, 259, 4317-4320. (b) Chen, L. H.; Borders, C. L.; Vasquez, J. R.; Kenyon, G. L. Biochemistry 1996, 35, 7895-7902. (c) Hurne, A. M.; Chai, C. L. L.; Waring, P. J. Biol. Chem. 2000, 275, 25202-25206.
(22) (a) Amos, R. A.; Fawcett, S. M. J. Org. Chem. 1984, 49, 2637-2639. (b) Woycechowsky, K. J.; Hook, B. A.; Raines, R. T. Biotechnol. Progr. 2003, 19, 1307-1314. (c) Bienvenu, C.; Greiner, J.; Vierling, P.; Di Giorgio, C. Tetrahedron Lett. 2010, 51, 3309-3311.
(23) Walker, J. M., Ed. The Protein Protocols Handbook, 3rd ed.; Humana Press: Totowa, N.J., 2009.
(24) (a) Ellman, G. L. Arch. Biochem. Biophys. 1958, 82, 70-77. (b) Riddles, P. W.; Blakely, R. L.; Zerner, B. Anal. Biochem. 1979, 94, 75-81. (c) Riddles, P. W.; Blakely, R. L.; Zerner, B. Method. Enzymol. 1983, 91, 49-60.

(25) Lees, W. J.; Singh, R.; Whitesides, G. M. J. Org. Chem. 1991, 56, 7328-7331.
(26) Simpson, R. J. Purifying Proteins for Proteomics: A Laboratory Manual; Cold Spring Harbor Laboratory Press: Cold Spring Harbor, N.Y., 2004.
(27) Mole, J. E.; Horton, H. R. Biochemistry 1973, 12, 816-822.
(28) Singh, R.; Whitesides, G. M. J. Org. Chem. 1991, 56, 2332-2337.
(29) Lee C.-H., Huang, H-C and Juan, H-F (2011) Reviewing Ligand-Based Rational Drug Design: The Search for an ATP Synthase Inhibitorint. J. Mol. Sci. 2011, 12, 5304-5318
(30) Peyrottes, S., Egron, D., Lefebvre, I., Gosselin, G., Imbach J.-L. and C. Périgaud (2004) SATE Pronucleotide Approaches: An Overview Mini-Reviews in Medicinal Chemistry 4:395-408.
(31) Perigaud, C.; Gosselin, G.; Imbach, J.-L. In Current Topics in Medicinal Chemistry; Alexander, J. C. Ed.; Blackwell Science Ltd: Oxford, 1997; Vol. 2, pp 15-29.
(32) Peyrottes, S., and Périgaud, C. (2007) Chemistry of bisSATE Mononucleotide Prodrugs Current Protocols in Nucleic Acid Chemistry (Supplment 29) unit 15.3 15.3.1-15.3.13
(33) Oetke, C. et al. (2002) Versatile Biosynthetic Engineering of Sialic Acid in Living Cells Using Synthetic Sialic Acid Analogues J. Biol. Chem. 277:6688-6695.
(34) Cumming, R. C. et al. (2004) Protein Disulfide Bond Formation in the Cytoplasm during Oxidative Stress J. Biol. Chem, 279:21749-21758.
(35) McCord, J. M. (1994) Science 266(5190):1586-1587.
(36) Furukawa, Y. et al. (2006) Proc. Nat'l Acad. Sci. USA 103(18):7148-7153.

We claim:
1. A compound having formula I or II:

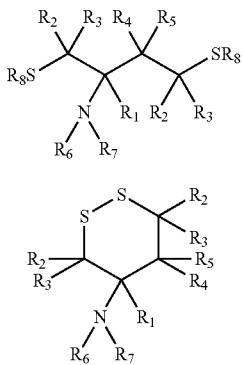

or salts thereof where:
R₁ is hydrogen, or an unsubstituted alkyl group having 1 to 3 carbon atoms;
each $R_2$ and $R_3$ is independently hydrogen, an alkyl group having 1-3 carbon atoms, a phenyl or a benzyl group each of which is optionally substituted with one or more of substituents $W_2$;
each $R_4$ and $R_5$ is hydrogen;
each $R_6$ and $R_7$ is independently hydrogen, a 1-12 carbon alkyl group, an aryl group, a heterocyclic group, a heteroaryl group, a —CO—NHR₁₁ group, a —CO—NHR₁₁ group, a —SO₂—R₁₁ group, or a —(CH₂)ₙ—R₁₂ group, wherein n is an integer ranging from 1-12 and each alkyl, aryl heterocylic or heteroaryl group is optionally substituted with one or more of substituents $W_3$; and
each $R_8$ is independently hydrogen or —CO—R₁₃,
wherein:
each $R_{11}$ and $R_{12}$ is independently hydrogen, a 1-12 carbon alkyl group, an aryl group, a heterocyclic group, a heteroaryl group, a -L-T group or a -M group, wherein each alkyl, aryl heterocylic or heteroaryl group is optionally substituted with one or more of substituents $W_3$, -L- is a divalent linker group and T is a biological species or a surface to which the reducing agent is linked and -M is a reactive group or a spacer moiety carrying a reactive group;
each $R_{13}$ is independently hydrogen, a 1-12 carbon alkyl group, an aryl group, a heterocyclic group, or a heteroaryl group, wherein each alkyl, aryl heterocyclic or heteroaryl group is optionally substituted with one or more of substituents $W_3$;
wherein;
$W_2$ is one or more substituents selected from halogen, an oxo group (═O), cyano group, nitro group, hydroxyl, unsubstituted alkyl group having 1-3 carbon atoms, halogen-substituted alkyl group having 1-3 carbon atoms, or unsubstituted alkoxy group having 1-3 carbon atoms; and
$W_3$ is one or more substituents selected from halogen, an oxo group (═O), cyano group, nitro group, hydroxyl, optionally substituted alkyl group having 1-6 carbon atoms, unsubstituted alkyl group having 1-6 carbon atoms, hydroxyl-substituted alkyl group having 1-6 carbon atoms, halogen-substituted alkyl group having 1-6 carbon atoms, unsubstituted alkoxy group having 1-6 carbon atoms, alkenyl group having 2-6 carbon atoms; alkynyl group having 2-6 carbon atoms, a 3-6-member alicyclic ring, wherein one or two ring carbons are optionally replaced with —CO— and which may contain one or two double bonds, an aryl group having 6-14 carbon ring atoms, a phenyl group, a benzyl group, a 5- or 6-member ring heterocyclic group having 1-3 heteroatoms and wherein one or two ring carbons are optionally replaced with —CO— and which may contain one or two double bonds, or a heteroaryl group having 1-3 heteroatoms (N, O or S), a —CO₂R₁₄ group, a —CON(R₁₅)₂ group, a —OCON(R₁₅)₂ group, a —N(R₁₅)₂ group, a —SO₂—OR₁₅ group, a —(CH₂)ₘ—OR₁₄ group, or a —(CH₂)ₘ—N(R₁₅)₂,
where m is 1-8, and
each $R_{14}$ and $R_{15}$ is independently hydrogen, an unsubstituted alkyl group having 1-6 carbon atoms; an unsubstituted aryl group having 6-14 carbon atoms, an unsubstituted phenyl group; an unsubstituted benzyl group, an unsubstituted 5- or 6-member ring heterocyclic group, having 1-3 heteroatoms and wherein one or two ring carbons are optionally replaced with —CO— and which may contain one or two double bonds, or a unsubstituted heteroaryl group having 1-3 heteroatoms, with the exception that no $R_{14}$ is hydrogen, and with the exception that in the compound of formula II not all of $R_1$-$R_7$ are hydrogen.

2. The compound of claim 1 wherein $R_1$, $R_2$ and $R_3$ are all hydrogens.
3. The compound of claim 1 wherein $R_1$, $R_2$, $R_3$, $R_4$ and $R_5$ are all hydrogens.
4. The compound of claim 1 wherein both $R_8$ are hydrogens.

5. The compound of claim 1 wherein both of $R_8$ are acyl groups.

6. The compound of claim 1 wherein one of $R_6$ or $R_7$ is an acyl group.

7. The compound of claim 1 wherein both of $R_6$ or $R_7$ are hydrogens.

8. The compound of claim 1 wherein $R_{11}$ or $R_{12}$ is -M.

9. The compound of claim 1 wherein $R_{11}$ or $R_{12}$ is -L-T.

10. The compound of claim 1 wherein $R_1$-$R_8$ are all hydrogens.

11. The compound of claim 1 wherein $R_1$-$R_7$ are all hydrogens and each $R_8$ is a —CO—$R_{13}$ wherein $R_{13}$ is an alkyl group having 1-6 carbon atoms, a halogen-substituted alkyl group having 1-6 carbon atoms, a hydroxy-substituted alkyl group having 1 to 6 carbon atoms, an optionally substituted phenyl group or an optionally substituted benzyl group.

12. The compound of claim 1 wherein $R_1$, $R_2$, $R_3$ and one of $R_4$ or $R_5$ are all hydrogens and the other of $R_4$ or $R_5$ is an optionally substituted alkyl group having 1-3 carbons atoms, a halogen, a hydroxyl, or an acyl group.

13. The compound of claim 1 having formula 1:

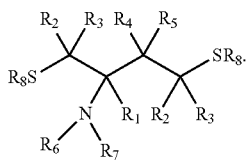

14. The compound of claim 1 which is non-racemic having formula:

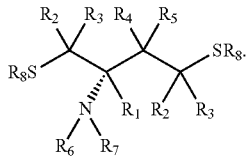

15. The compound of claim 14 wherein $R_1$-$R_3$ are all hydrogens.

16. A compound of formula:

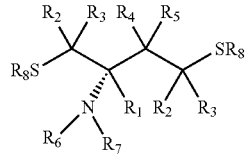

or salts thereof,
wherein $R_1$-$R_7$ are all hydrogens, each $R_8$ is hydrogen or —CO—$R_{13}$, and each $R_{13}$ is independently hydrogen, a 1-12 carbon alkyl group, an aryl group, a heterocyclic group, or a heteroaryl group, wherein each alkyl, aryl heterocyclic or heteroaryl group is optionally substituted with one or more of substituents $W_3$;

$W_3$ is one or more substituents selected from halogen, an oxo group (=O), cyano group, nitro group, hydroxyl, optionally substituted alkyl group having 1-6 carbon atoms, unsubstituted alkyl group having 1-6 carbon atoms, hydroxyl-substituted alkyl group having 1-6 carbon atoms, halogen-substituted alkyl group having 1-6 carbon atoms, unsubstituted alkoxy group having 1-6 carbon atoms, alkenyl group having 2-6 carbon atoms; alkynyl group having 2-6 carbon atoms, a 3-6-member alicyclic ring, wherein one or two ring carbons are optionally replaced with —CO— and which may contain one or two double bonds, an aryl group having 6-14 carbon ring atoms, a phenyl group, a benzyl group, a 5- or 6-member ring heterocyclic group having 1-3 heteroatoms and wherein one or two ring carbons are optionally replaced with —CO— and which may contain one or two double bonds, or a heteroaryl group having 1-3 heteroatoms (N, O or S), a —CO$_2$R$_{14}$ group, a —CON(R$_{15}$)$_2$ group, a —OCON(R$_{15}$)$_2$ group, a —N(R$_{15}$)$_2$ group, a —SO$_2$—OR$_{15}$ group, —(CH$_2$)$_m$—OR$_{14}$ group, or —(CH$_2$)$_m$—N(R$_{15}$)$_2$, where m is 1-8, and each $R_{14}$ and $R_{15}$ is independently hydrogen; an unsubstituted alkyl group having 1-6 carbon atoms; an unsubstituted aryl group having 6-14 carbon atoms; an unsubstituted phenyl group; an unsubstituted benzyl group; an unsubstituted 5- or 6-member ring heterocyclic group, having 1-3 heteroatoms and wherein one or two ring carbons are optionally replaced with —CO— and which may contain one or two double bonds; or a unsubstituted heteroaryl group having 1-3 heteroatoms; with the exception that no $R_{14}$ is hydrogen.

17. The compound of claim 16 wherein each $R_8$ is a hydrogen.

18. The compound of claim 16 wherein $R_8$ are both acyl groups.

19. The compound of claim 16 which is covalently conjugated to a surface.

20. The compound of claim 16 which is covalently conjugated to a peptide, protein, carbohydrate or a nucleic acid.

21. The compound of claim 1 which is covalently conjugated to a ligand which binds to a peptide or protein or a substrate of an enzyme.

22. The compound of claim 16 wherein each $R_8$ is hydrogen or —CO—$R_{13}$, and each $R_{13}$ is independently hydrogen, a 1-12 carbon alkyl group, or an aryl group.

23. A kit comprising one or more of the compounds of claim 1 in combination with one or more components selected from one or more molecules having one or more sulfhydryl groups, or one or more solvents or buffers for the one or more molecules or one or more compounds.

24. The kit of claim 23 for reducing or preventing disulfide bond formation comprising one or more of the compounds of formula I of claim 1.

25. A method for reducing or preventing disulfide bond formation in one or more molecules having one or more sulfhydryl group, other than a compound of formula I, which comprises the step of contacting the one or more molecules with one or more compounds of formula I of claim 1.

26. The method of claim 25 wherein the contacting is carried out at a pH ranging from 6-8.

27. The method of claim 25 wherein the contacting is carried out at a pH ranging from 6.5 to 7.5.

28. The method of claim 25 wherein the one or more compounds are covalently attached to a surface.

29. The method of claim 25 wherein both $R_8$ of the one or more compounds are acyl groups and the acyl groups of the compound are removed prior to or at the same time as the contacting.

30. The method of claim 25 wherein reducing or preventing disulfide bond formation reduces or prevents the formation of dimers or other oligomers of the one or more molecules having sulfhydryl groups.

31. The method of claim 25 wherein the molecules having one or more sulfhydryl groups are peptides or proteins and reducing or preventing disulfide bond formation functions to modulate a biological activity of the one or more peptides or proteins.

\* \* \* \* \*